(12) United States Patent
Shao et al.

(10) Patent No.: US 8,956,620 B2
(45) Date of Patent: Feb. 17, 2015

(54) ANTI-HIV VACCINE CONSTRUCTED BASED ON AMINO ACID MUTATIONS IN ATTENUATED LIVE EIAV VACCINE

(75) Inventors: Yiming Shao, Beijing (CN); Lianxing Liu, Beijing (CN); Rongxian Shen, Harbin (CN)

(73) Assignee: National Center for AIDS/STD Control and Prevention, Chinese Center for Disease Control and Prevention, Beijing (CN)

( * ) Notice: Subject to any disclaimer, the term of this patent is extended or adjusted under 35 U.S.C. 154(b) by 672 days.

(21) Appl. No.: 12/994,758

(22) PCT Filed: May 27, 2009

(86) PCT No.: PCT/CN2009/072017
§ 371 (c)(1),
(2), (4) Date: Nov. 24, 2010

(87) PCT Pub. No.: WO2009/143775
PCT Pub. Date: Dec. 3, 2009

(65) Prior Publication Data
US 2011/0195084 A1    Aug. 11, 2011

(30) Foreign Application Priority Data
May 27, 2008   (CN) .......................... 2008 1 0097471

(51) Int. Cl.
*A61K 39/00* (2006.01)
*A61K 39/12* (2006.01)
*A61K 39/21* (2006.01)
*A61K 38/00* (2006.01)
*C07K 14/005* (2006.01)
*C07K 16/10* (2006.01)

(52) U.S. Cl.
CPC ............... *A61K 39/21* (2013.01); *C07K 14/005* (2013.01); *C07K 16/1063* (2013.01); *A61K 2039/5254* (2013.01); *A61K 2039/5256* (2013.01); *A61K 2039/53* (2013.01); *C12N 2740/16122* (2013.01); *C12N 2740/16134* (2013.01)
USPC .................. 424/188.1; 424/184.1; 424/185.1; 424/186.1; 424/187.1; 514/1.1

(58) Field of Classification Search
None
See application file for complete search history.

(56) References Cited

U.S. PATENT DOCUMENTS

2002/0146683 A1 * 10/2002 Barnett et al. .................... 435/5

OTHER PUBLICATIONS

Zheng, et al. (2001, EMBL assession #U8UL89).*
Derdeyn, et al. (Envelope-constrained neutralization-sensitive HIV-1 after heterosexual transmission. Science. 2004; 303:2019-2022).*
Derdeyn, et al. (2004, EMBL assession #Q6TCN0).*
Monken, et al. (High resolution analysis of HIV-1 quasispecies in the brain. AIDS. 1995; 9:345-349).*
Monken et al. (EMBL assession #Q76096).*
Levine. Why Do We Not Yet Have a Human Immunodeficiency Virus Vaccine? J. Virol. 2008; 82(24): 11998-12000.*
Cohen. Promising AIDS Vaccine's Failure Leaves Field Reeling. Science. 2007; 318:28.*

* cited by examiner

*Primary Examiner* — Zachariah Lucas
*Assistant Examiner* — Stuart W Snyder
(74) *Attorney, Agent, or Firm* — Alston & Bird LLP

(57) ABSTRACT

Provided are antigenic polypeptides of HIV envelope glycoproteins which are constructed based on amino acid mutation of attenuated live vaccine of Equine Infectious Anemia Virus, DNA constructions and recombinant virus vectors comprising polynucleotides encoding said polypeptides, antibodies against said polypeptides as well as uses thereof in preventing and treating HIV infection. Said antigenic polypeptides and vaccines can induce high titer neutralization antibodies against HIV in organism.

12 Claims, 6 Drawing Sheets ions in HIV. However, these vaccines have failed to protect vaccines from HIV infection. The third generation (2000-2005) of HIV candidate vaccines was based on the feature of different vaccine vectors and strategy to proceed carefully to expanded phase II and phase III trials to assess the protective efficacy of these candidate vaccines in humans. The new concept is based on inducing potent immune response by HIV conserved epitopes.

SEQUENCE LISTING

```
<160> NUMBER OF SEQ ID NOS: 18

<210> SEQ ID NO 1
<211> LENGTH: 856
<212> TYPE: PRT
<213> ORGANISM: Human immunodeficiency virus type 1
<220> FEATURE:
<223> OTHER INFORMATION: Amino acid sequence of HIV-1 HXB2 gp160

<400> SEQUENCE: 1

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110
```

```
Asp Gln Ser Leu Lys Pro Cys Val Lys Leu Thr Pro Leu Cys Val Ser
            115                 120                 125
Leu Lys Cys Thr Asp Leu Lys Asn Asp Thr Asn Thr Asn Ser Ser Ser
        130                 135                 140
Gly Arg Met Ile Met Glu Lys Gly Glu Ile Lys Asn Cys Ser Phe Asn
145                 150                 155                 160
Ile Ser Thr Ser Ile Arg Gly Lys Val Gln Lys Glu Tyr Ala Phe Phe
                165                 170                 175
Tyr Lys Leu Asp Ile Ile Pro Ile Asp Asn Asp Thr Thr Ser Tyr Lys
            180                 185                 190
Leu Thr Ser Cys Asn Thr Ser Val Ile Thr Gln Ala Cys Pro Lys Val
        195                 200                 205
Ser Phe Glu Pro Ile Pro Ile His Tyr Cys Ala Pro Ala Gly Phe Ala
    210                 215                 220
Ile Leu Lys Cys Asn Asn Lys Thr Phe Asn Gly Thr Gly Pro Cys Thr
225                 230                 235                 240
Asn Val Ser Thr Val Gln Cys Thr His Gly Ile Arg Pro Val Val Ser
                245                 250                 255
Thr Gln Leu Leu Leu Asn Gly Ser Leu Ala Glu Glu Val Val Ile
            260                 265                 270
Arg Ser Val Asn Phe Thr Asp Asn Ala Lys Thr Ile Ile Val Gln Leu
        275                 280                 285
Asn Thr Ser Val Glu Ile Asn Cys Thr Arg Pro Asn Asn Thr Arg
    290                 295                 300
Lys Arg Ile Arg Ile Gln Arg Gly Pro Gly Arg Ala Phe Val Thr Ile
305                 310                 315                 320
Gly Lys Ile Gly Asn Met Arg Gln Ala His Cys Asn Ile Ser Arg Ala
                325                 330                 335
Lys Trp Asn Asn Thr Leu Lys Gln Ile Ala Ser Lys Leu Arg Glu Gln
            340                 345                 350
Phe Gly Asn Asn Lys Thr Ile Ile Phe Lys Gln Ser Ser Gly Gly Asp
        355                 360                 365
Pro Glu Ile Val Thr His Ser Phe Asn Cys Gly Gly Glu Phe Phe Tyr
    370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
                405                 410                 415
Pro Cys Arg Ile Lys Gln Ile Ile Asn Met Trp Gln Lys Val Gly Lys
            420                 425                 430
Ala Met Tyr Ala Pro Pro Ile Ser Gly Gln Ile Arg Cys Ser Ser Asn
        435                 440                 445
Ile Thr Gly Leu Leu Leu Thr Arg Asp Gly Gly Asn Ser Asn Asn Glu
    450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Lys Ala Lys Arg Arg Val Val Gln Arg Glu Lys Arg Ala
            500                 505                 510
Val Gly Ile Gly Ala Leu Phe Leu Gly Phe Leu Gly Ala Ala Gly Ser
        515                 520                 525
Thr Met Gly Ala Ala Ser Met Thr Leu Thr Val Gln Ala Arg Gln Leu
```

```
                    530                 535                 540
Leu Ser Gly Ile Val Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
                595                 600                 605

Pro Trp Asn Ala Ser Trp Ser Asn Lys Ser Leu Glu Gln Ile Trp Asn
610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
                660                 665                 670

Phe Asn Ile Thr Asn Trp Leu Trp Tyr Ile Lys Leu Phe Ile Met Ile
            675                 680                 685

Val Gly Gly Leu Val Gly Leu Arg Ile Val Phe Ala Val Leu Ser Ile
690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
                740                 745                 750

Leu Ala Leu Ile Trp Asp Asp Leu Arg Ser Leu Cys Leu Phe Ser Tyr
            755                 760                 765

His Arg Leu Arg Asp Leu Leu Leu Ile Val Thr Arg Ile Val Glu Leu
        770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
                820                 825                 830

Val Gln Gly Ala Cys Arg Ala Ile Arg His Ile Pro Arg Arg Ile Arg
            835                 840                 845

Gln Gly Leu Glu Arg Ile Leu Leu
850                 855

<210> SEQ ID NO 2
<211> LENGTH: 699
<212> TYPE: PRT
<213> ORGANISM: Human immunodeficiency virus type 1
<220> FEATURE:
<223> OTHER INFORMATION: Amino acid sequence of HIV-1 CN54 gp145

<400> SEQUENCE: 2

Met Asp Arg Ala Lys Leu Leu Leu Leu Leu Leu Leu Leu Leu Leu Pro
1               5                   10                  15

Gln Ala Gln Ala Val Gly Asn Leu Trp Val Thr Val Tyr Tyr Gly Val
                20                  25                  30

Pro Val Trp Lys Gly Ala Thr Thr Thr Leu Phe Cys Ala Ser Asp Ala
```

```
                35                  40                  45
Lys Ala Tyr Asp Thr Glu Val His Asn Val Trp Ala Thr His Ala Cys
            50                  55                  60
Val Pro Ala Asp Pro Asn Pro Gln Glu Met Val Leu Glu Asn Val Thr
 65                  70                  75                  80
Glu Asn Phe Asn Met Trp Lys Asn Glu Met Val Asn Gln Met Gln Glu
                 85                  90                  95
Asp Val Ile Ser Leu Trp Asp Gln Ser Leu Lys Pro Cys Val Lys Leu
            100                 105                 110
Thr Pro Leu Cys Val Thr Leu Glu Cys Arg Asn Val Ser Ser Asn Ser
        115                 120                 125
Asn Asp Thr Tyr His Glu Thr Tyr His Glu Ser Met Lys Glu Met Lys
    130                 135                 140
Asn Cys Ser Phe Asn Ala Thr Thr Val Val Arg Asp Arg Lys Gln Thr
145                 150                 155                 160
Val Tyr Ala Leu Phe Tyr Arg Leu Asp Ile Val Pro Leu Thr Lys Lys
                165                 170                 175
Asn Tyr Ser Glu Asn Ser Ser Glu Tyr Tyr Arg Leu Ile Asn Cys Asn
            180                 185                 190
Thr Ser Ala Ile Thr Gln Ala Cys Pro Lys Val Thr Phe Asp Pro Ile
        195                 200                 205
Pro Ile His Tyr Cys Thr Pro Ala Gly Tyr Ala Ile Leu Lys Cys Asn
    210                 215                 220
Asp Lys Ile Phe Asn Gly Thr Gly Pro Cys His Asn Val Ser Thr Val
225                 230                 235                 240
Gln Cys Thr His Gly Ile Lys Pro Val Val Ser Thr Gln Leu Leu Leu
                245                 250                 255
Asn Gly Ser Leu Ala Glu Gly Glu Ile Ile Ile Arg Ser Glu Asn Leu
            260                 265                 270
Thr Asn Asn Val Lys Thr Ile Ile Val His Leu Asn Gln Ser Val Glu
        275                 280                 285
Ile Val Cys Thr Arg Pro Gly Asn Asn Thr Arg Lys Ser Ile Arg Ile
    290                 295                 300
Gly Pro Gly Gln Thr Phe Tyr Ala Thr Gly Asp Ile Ile Gly Asp Ile
305                 310                 315                 320
Arg Gln Ala His Cys Asn Ile Ser Glu Asp Lys Trp Asn Glu Thr Leu
                325                 330                 335
Gln Arg Val Ser Lys Lys Leu Ala Glu His Phe Gln Asn Lys Thr Ile
            340                 345                 350
Lys Phe Ala Ser Ser Ser Gly Gly Asp Leu Glu Val Thr Thr His Ser
        355                 360                 365
Phe Asn Cys Arg Gly Glu Phe Phe Tyr Cys Asn Thr Ser Gly Leu Phe
    370                 375                 380
Asn Gly Ala Tyr Thr Pro Asn Gly Thr Lys Ser Asn Ser Ser Ser Ile
385                 390                 395                 400
Ile Thr Ile Pro Cys Arg Ile Lys Gln Ile Ile Asn Met Trp Gln Glu
                405                 410                 415
Val Gly Arg Ala Met Tyr Ala Pro Pro Ile Lys Gly Asn Ile Thr Cys
            420                 425                 430
Lys Ser Asn Ile Thr Gly Leu Leu Leu Val Arg Asp Gly Gly Thr Glu
        435                 440                 445
Pro Asn Asp Thr Glu Thr Phe Arg Pro Gly Gly Gly Asp Met Arg Asn
    450                 455                 460
```

```
Asn Trp Arg Ser Glu Leu Tyr Lys Tyr Lys Val Val Glu Ile Lys Pro
465                 470                 475                 480

Leu Gly Val Ala Pro Thr Thr Lys Arg Val Val Glu Arg Glu
            485                 490                 495

Lys Arg Ala Val Gly Ile Gly Ala Val Phe Leu Gly Phe Leu Gly Val
                500                 505                 510

Ala Gly Ser Thr Met Gly Ala Ala Ser Ile Thr Leu Thr Val Gln Ala
            515                 520                 525

Arg Gln Leu Leu Ser Gly Ile Val Gln Gln Ser Asn Leu Leu Arg
            530                 535                 540

Ala Ile Glu Ala Gln Gln His Leu Leu Gln Leu Thr Val Trp Gly Ile
545                 550                 555                 560

Lys Gln Leu Gln Thr Arg Val Leu Ala Ile Glu Arg Tyr Leu Lys Asp
                565                 570                 575

Gln Gln Leu Leu Gly Ile Trp Gly Cys Ser Gly Lys Leu Ile Cys Thr
            580                 585                 590

Thr Ala Val Pro Trp Asn Ser Ser Trp Ser Asn Lys Ser Gln Lys Glu
            595                 600                 605

Ile Trp Asp Asn Met Thr Trp Met Gln Trp Asp Lys Glu Ile Ser Asn
610                 615                 620

Tyr Thr Asn Thr Val Tyr Arg Leu Leu Glu Glu Ser Gln Asn Gln Gln
625                 630                 635                 640

Glu Arg Asn Glu Lys Asp Leu Leu Ala Leu Asp Ser Trp Lys Asn Leu
                645                 650                 655

Trp Ser Trp Phe Asp Ile Thr Asn Trp Leu Trp Tyr Ile Lys Ile Phe
            660                 665                 670

Ile Ile Ile Val Gly Gly Leu Ile Gly Leu Arg Ile Ile Phe Ala Val
            675                 680                 685

Leu Ser Ile Val Asn Arg Val Arg Gln Gly Tyr
            690                 695

<210> SEQ ID NO 3
<211> LENGTH: 865
<212> TYPE: PRT
<213> ORGANISM: Equine infectious anemia virus
<220> FEATURE:
<223> OTHER INFORMATION: Amino acid sequence of EIAV LN strain envelope
      protein

<400> SEQUENCE: 3

Met Val Ser Ile Ala Phe Tyr Gly Gly Ile Pro Gly Gly Ile Ser Thr
1               5                   10                  15

Pro Ile Thr Gln Gln Thr Glu Ser Thr Asp Thr Gln Lys Gly Asp His
                20                  25                  30

Met Val Tyr Gln Pro Tyr Cys Tyr Asn Asp Ser His Lys Ala Glu Met
            35                  40                  45

Ala Glu Ala Arg Asp Thr Arg Tyr Gln Glu Met Asn Arg Lys Glu
            50                  55                  60

Glu Lys Glu Asp Asn Lys Arg Arg Asn Asn Trp Trp Lys Ile Gly Met
65                  70                  75                  80

Phe Leu Leu Cys Leu Leu Gly Thr Gly Gly Phe Leu Trp Trp Tyr
                85                  90                  95

Glu Gly Gln Lys His Ser His Tyr Ile Gly Leu Val Thr Ile Gly Ser
                100                 105                 110

Arg Leu Asn Gly Ser Gly Met Thr Ser Ala Ile Glu Cys Trp Gly Ser
```

```
            115                 120                 125
Phe Pro Gly Cys Arg Pro Phe Thr Asn Tyr Phe Ser Tyr Glu Thr Asn
130                 135                 140

Arg Thr Ile Ser Arg Asp Asn Asn Thr Ala Thr Leu Leu Asp Ala Tyr
145                 150                 155                 160

Gln Arg Glu Val Thr Asn Ile Tyr Arg Thr Ser Cys Val Asp Ser Asp
                165                 170                 175

His Cys Gln Glu Tyr Lys Cys Lys Gln Val Gln Leu Lys Glu Asn Ser
                180                 185                 190

Ser Asn Ile Ile Met Asn Asn Cys Ser Asn Ser Cys Glu Glu Phe
                195                 200                 205

Trp Gly Phe Ser Trp Leu Glu Cys Asn Gln Thr Glu Asn Ala Ile Thr
                210                 215                 220

Ile Leu Val Pro Glu Val Glu Met Gln Gln Ser Asp Asn Asn Thr Trp
225                 230                 235                 240

Ile Pro Lys Arg Cys Asn Glu Thr Trp Ala Arg Val Lys His Cys Pro
                245                 250                 255

Met Asp Leu Leu Tyr Gly Ile Asn Arg Ile Arg Met Cys Val Gln Pro
                260                 265                 270

Pro Phe Phe Leu Phe Lys Gln Asn Asp Thr Ser Asn Thr Ser Ile
                275                 280                 285

Leu Ser Asn Cys Gly Pro Leu Val Phe Leu Gly Ile Leu Glu Asp Asn
290                 295                 300

Lys Ala Ala Ile Gln Asn Gly Ser Cys Thr Leu His Arg Thr Asn Ile
305                 310                 315                 320

Lys Arg Pro Asp Tyr Ser Gly Phe Tyr Gln Val Pro Ile Phe Tyr Ile
                325                 330                 335

Cys Asn Leu Thr Gly Leu Gln Ser Cys Asn Asn Gly Ser Ile Ile Ser
                340                 345                 350

Ile Ile Met Ser Glu Ser Asn Asn Val Gln Tyr Leu Leu Cys Asn Thr
                355                 360                 365

Ser Asn Thr Asn Ser Thr Asn Asn Ala Thr Val Ser Cys Val Val Gln
370                 375                 380

Ser Phe Gly Val Ile Gly Gln Ala His Val Ala Leu Pro Arg Lys Asn
385                 390                 395                 400

Lys Arg Leu Gln Ser Pro Lys Phe Ala His Tyr Asn Cys Thr Ile Asn
                405                 410                 415

Asn Lys Thr Glu Leu Arg Gln Trp Gln Leu Val Lys Thr Ser Gly Ile
                420                 425                 430

Thr Pro Leu Pro Ile Ser Ser Thr Ala Asn Thr Gly Leu Val Arg His
                435                 440                 445

Lys Arg Asp Phe Gly Ile Ser Ala Ile Ile Ala Ala Ile Val Ala Ala
                450                 455                 460

Thr Ala Ile Ala Ala Ser Val Thr Met Ser Tyr Ile Ala Leu Thr Asp
465                 470                 475                 480

Val Asn Lys Leu Asp Ser Val Gln Asn His Thr Phe Glu Val Glu Asn
                485                 490                 495

Asn Thr Ile Asn Gly Leu Glu Leu Val Glu Glu Gln Ile His Ile Leu
                500                 505                 510

Tyr Ala Met Val Leu Gln Thr His Ala Asp Val Gln Leu Leu Lys Glu
                515                 520                 525

Gln Gln Lys Ile Glu Glu Thr Phe Asn Leu Ile Gly Cys Ile Glu Arg
530                 535                 540
```

```
Ser His Thr Phe Cys His Thr Gly His Pro Trp Asn Glu Ser Trp Gly
545                 550                 555                 560

Gln Leu Asn Asp Ser Thr Gln Trp Asp Asp Trp Val Asp Lys Met Glu
                565                 570                 575

Asn Leu Asn His Asp Ile Leu Thr Thr Leu His Thr Ala Arg Asn Asn
                580                 585                 590

Leu Glu Gln Ser Met Ile Thr Phe Asn Thr Pro Asp Ser Ile Ala Gln
                595                 600                 605

Phe Gly Lys Asn Ile Trp Ser His Ile Ala Asn Trp Ile Pro Gly Leu
610                 615                 620

Gly Ala Ser Ile Ile Lys Tyr Ile Val Leu Leu Leu Val Tyr Val
625                 630                 635                 640

Leu Leu Thr Ser Ala Pro Lys Ile Leu Arg Gly Leu Leu Thr Thr Met
                645                 650                 655

Ser Gly Ala Gly Ser Ser Ala Ser Arg Tyr Leu Arg Lys Arg Tyr His
                660                 665                 670

His Arg His Ala Ser Arg Gly Asp Ile Trp Ala Gln Val Gln Tyr His
                675                 680                 685

Ala Tyr Leu Ala Asp Glu Thr His Gly Ser Gly Asp Lys Ser Asn Met
690                 695                 700

Arg Lys Leu Ser Arg Asn Asn Trp Asn Gly Glu Ser Glu Tyr Asn
705                 710                 715                 720

Arg Arg Gln Lys Asn Trp Lys Lys Leu Ile Lys Arg Ser Gly Glu Asn
                725                 730                 735

Tyr Asn Thr His Glu Asp Asn Met Gly Thr Met Gly Arg Leu Val Thr
                740                 745                 750

Thr Ala Ala Glu Lys Lys Asn Val Gly Val Asn Pro His Gln Gly Ser
                755                 760                 765

Leu Asn Leu Glu Ile Gln Ser Glu Gly Gly Asn Ile Tyr Asp Cys Cys
770                 775                 780

Ile Lys Ala Gln Glu Gly Thr Leu Ala Ile Pro Cys Cys Gly Phe Pro
785                 790                 795                 800

Leu Trp Leu Leu Trp Gly Leu Ile Ile Leu Gly Arg Leu Leu Gly
                805                 810                 815

Tyr Gly Leu Arg Gly Ile Ala Lys Ile Ile Met Ile Leu Gly Lys Gly
                820                 825                 830

Leu Asn Val Ile Ile Thr Gly Leu Arg Lys Leu Cys Asp Tyr Ile Gly
                835                 840                 845

Lys Met Leu Asn Pro Ala Thr Ser His Val Thr Met Pro Gln Tyr Asp
850                 855                 860

Val
865

<210> SEQ ID NO 4
<211> LENGTH: 864
<212> TYPE: PRT
<213> ORGANISM: Equine infectious anemia virus
<220> FEATURE:
<223> OTHER INFORMATION: Amino acid sequence of EIAV D510 strain
      envelope protein

<400> SEQUENCE: 4

Met Val Ser Ile Ala Phe Tyr Gly Gly Ile Pro Gly Gly Val Ser Thr
1               5                   10                  15

Pro Ile Thr Gln Gln Thr Glu Ser Thr Asp Thr Gln Lys Gly Asp His
```

-continued

```
                20                  25                  30
Met Val Tyr Gln Pro Tyr Cys Tyr Asn Asp Ser His Lys Ala Glu Met
             35                  40                  45
Ala Glu Ala Arg Gly Thr Arg Tyr Gln Glu Glu Met Asn Arg Lys Glu
     50                  55                  60
Asp Lys Glu Asp Lys Arg Arg Asn Asn Trp Trp Lys Ile Gly Met Phe
 65                  70                  75                  80
Leu Leu Cys Leu Leu Gly Thr Thr Gly Phe Leu Trp Trp Tyr Glu
                 85                  90                  95
Gly Gln His His Ser His Tyr Ile Gly Leu Val Thr Ile Gly Gly Arg
             100                 105                 110
Leu Asn Gly Ser Gly Met Thr Ser Ala Ile Glu Cys Trp Gly Ser Phe
         115                 120                 125
Pro Gly Cys Arg Pro Phe Thr Asn Tyr Phe Ser Tyr Glu Thr Asn Arg
         130                 135                 140
Thr Val Ser Arg Asp Asn Asn Thr Ala Thr Leu Leu Asp Ala Tyr Gln
145                 150                 155                 160
Arg Glu Ile Thr Asn Ile Tyr Arg Thr Ser Cys Val Asp Ser Asp His
                 165                 170                 175
Cys Gln Glu Tyr Lys Cys Lys Gln Val Gln Leu Lys Glu Asn Ser Ser
             180                 185                 190
Asn Ile Ile Met Asn Asn Cys Ser Ser Asn Ser Cys Glu Glu Phe Arg
         195                 200                 205
Gly Phe Ser Trp Leu Glu Cys Asn Gln Thr Glu Asn Ala Ile Thr Ile
         210                 215                 220
Leu Val Pro Asp Ile Glu Met Gln Glu Ser Asp Asn Asn Thr Trp Ile
225                 230                 235                 240
Pro Lys Arg Cys Asn Glu Thr Trp Ala Arg Val Lys His Cys Pro Met
                 245                 250                 255
Asp Leu Leu Tyr Gly Ile Asn Arg Ile Arg Met Cys Val Gln Pro Pro
             260                 265                 270
Phe Phe Leu Phe Lys Gln Asn Asp Thr Ser Asn Asn Thr Gly Ile Leu
         275                 280                 285
Ser Asn Cys Gly Pro Leu Val Phe Leu Gly Ile Leu Glu Asp Asn Lys
         290                 295                 300
Ala Ala Val Gln Asn Gly Ser Cys Thr Leu His Arg Thr Asn Ile Lys
305                 310                 315                 320
Arg Pro Asp Tyr Ser Gly Phe Tyr Gln Val Pro Ile Phe Tyr Ile Cys
                 325                 330                 335
Asn Leu Thr Gly Leu Gln Ser Cys Asn Asn Gly Ser Ile Ile Ser Ile
             340                 345                 350
Ile Met Tyr Glu Ser Asn Asn Val Gln Tyr Leu Leu Cys Asn Thr Ser
         355                 360                 365
Asn Thr Asn Ser Thr Asn Asn Ala Asn Val Ser Cys Val Val Gln Ser
         370                 375                 380
Phe Gly Val Ile Gly Gln Ala His Val Ala Leu Pro Arg Lys Asn Lys
385                 390                 395                 400
Arg Leu Gln Ser Pro Lys Phe Ala His Tyr Asn Cys Ser Ile Asn Asn
                 405                 410                 415
Lys Thr Glu Leu Arg Gln Trp Gln Leu Val Lys Thr Ser Gly Ile Thr
             420                 425                 430
Pro Leu Pro Ile Ser Ser Thr Ala Asn Thr Gly Leu Val Arg His Lys
         435                 440                 445
```

```
Arg Asp Phe Gly Ile Ser Ala Ile Ala Ala Ile Val Ala Ala Thr
450                 455                 460
Ala Ile Ala Ala Ser Ala Thr Met Ser Tyr Ile Ala Leu Thr Glu Val
465                 470                 475                 480
Asn Lys Leu Asp Ser Val Gln Asn His Thr Phe Glu Val Glu Asn Asn
            485                 490                 495
Thr Ile Asn Ser Met Glu Leu Ile Glu Glu Gln Ile His Ile Leu Tyr
                500                 505                 510
Ala Met Val Leu Gln Thr His Ala Asp Val Gln Leu Leu Lys Glu Gln
            515                 520                 525
Gln Lys Ile Glu Glu Thr Phe Asn Leu Ile Gly Cys Ile Glu Arg Ser
530                 535                 540
His Thr Phe Cys His Thr Gly His Pro Trp Asn Glu Ser Trp Gly Gln
545                 550                 555                 560
Leu Asn Asp Ser Thr Gln Trp Asp Asp Trp Val Asn Lys Met Glu Asn
                565                 570                 575
Leu Asn His Asp Ile Leu Thr Thr Leu His Thr Ala Arg Asn Asn Leu
            580                 585                 590
Asp Gln Ser Met Ile Thr Phe Asn Thr Pro Asp Ser Ile Ala Gln Phe
    595                 600                 605
Gly Lys Asn Ile Trp Ser His Ile Ala Asn Trp Ile Pro Gly Leu Gly
610                 615                 620
Ala Ser Ile Ile Lys Tyr Ile Val Leu Leu Leu Leu Val Tyr Val Leu
625                 630                 635                 640
Leu Thr Ser Ala Pro Lys Ile Leu Arg Gly Leu Leu Thr Thr Met Ser
                645                 650                 655
Gly Ala Gly Ser Ser Ala Ser Arg Tyr Leu Arg Lys Arg Tyr His His
            660                 665                 670
Arg His Ala Ser Arg Gly Asp Ile Trp Ala Gln Val Gln Tyr His Ala
    675                 680                 685
Tyr Leu Ala Asp Glu Thr His Gly Ser Gly Asp Lys Ser Asn Met Arg
690                 695                 700
Lys Leu Ser Arg Asn Asn Trp Asn Gly Glu Ser Glu Glu Tyr Asn Arg
705                 710                 715                 720
Arg Gln Lys Asn Trp Lys Arg Leu Ile Lys Arg Ser Gly Glu Asn Tyr
                725                 730                 735
Asn Thr His Glu Asp Asn Met Gly Thr Met Gly His Leu Ile Thr Thr
            740                 745                 750
Ala Ala Glu Lys Lys Asn Val Gly Glu Asn Pro His Gln Gly Ser Leu
    755                 760                 765
Asn Leu Glu Ile Gln Ser Glu Gly Gly Asn Ile Tyr Asp Cys Cys Ile
770                 775                 780
Lys Ala Gln Glu Gly Thr Leu Ala Ile Pro Cys Cys Gly Phe Pro Leu
785                 790                 795                 800
Trp Leu Leu Trp Gly Leu Ile Ile Ile Leu Gly Arg Leu Leu Gly Tyr
                805                 810                 815
Gly Leu Arg Gly Ile Ala Lys Ile Ile Thr Ile Leu Gly Lys Gly Leu
            820                 825                 830
Asn Val Ile Ile Thr Gly Leu Arg Lys Leu Cys Asp Tyr Ile Gly Lys
    835                 840                 845
Met Leu Asn Pro Ala Thr Ser His Val Thr Met Pro Gln Tyr Asp Val
850                 855                 860
```

<210> SEQ ID NO 5
<211> LENGTH: 863
<212> TYPE: PRT
<213> ORGANISM: Equine infectious anemia virus
<220> FEATURE:
<223> OTHER INFORMATION: Amino acid sequence of EIAV DLV strain envelope protein

<400> SEQUENCE: 5

```
Met Val Ser Ile Thr Phe Tyr Gly Gly Ile Pro Gly Gly Ile Ser Thr
1               5                   10                  15

Pro Ile Thr Gln Gln Thr Glu Ser Thr Asp Thr Gln Lys Gly Asp His
            20                  25                  30

Met Val Tyr Gln Pro Tyr Cys Tyr Asn Asp Ser His Lys Glu Glu Met
        35                  40                  45

Ala Glu Thr Arg Asp Thr Arg Tyr Gln Glu Glu Met Asn Arg Lys Glu
    50                  55                  60

Asp Lys Glu Asp Lys Arg Lys Asn Asn Trp Trp Lys Ile Gly Met Phe
65                  70                  75                  80

Leu Leu Cys Leu Leu Glu Ile Thr Gly Gly Phe Leu Trp Trp Tyr Glu
                85                  90                  95

Arg Gln Gln His Ser Tyr Tyr Ile Arg Leu Val Thr Ile Gly Gly Arg
            100                 105                 110

Leu Asn Gly Ser Gly Met Thr Ser Ala Ile Lys Cys Trp Gly Ser Phe
        115                 120                 125

Pro Gly Cys Arg Pro Phe Thr Asn Tyr Phe Ser Tyr Glu Thr Asn Arg
    130                 135                 140

Thr Val Ser Arg Asp Asn Asn Thr Ala Thr Leu Leu Asp Thr Tyr Gln
145                 150                 155                 160

Arg Glu Ile Thr Asn Ile Tyr Arg Thr Ser Cys Val Asp Ser Asp His
                165                 170                 175

Cys Gln Glu Tyr Lys Cys Lys Gln Val Gln Leu Lys Lys Asn Ser Asn
            180                 185                 190

Asn Ile Ile Met Asn Asn Cys Ser Asn Asn Arg Cys Glu Glu Phe Trp
        195                 200                 205

Gly Phe Ser Trp Leu Glu Cys Asn Gln Thr Glu Asn Ala Ile Thr Ile
    210                 215                 220

Leu Val Pro Glu Ile Glu Ile Gln Gln Arg Lys Asn Thr Trp Ile Pro
225                 230                 235                 240

Lys Arg Cys Glu Lys Thr Trp Ala Lys Val Lys His Cys Pro Met Asp
                245                 250                 255

Leu Leu Tyr Gly Ile Asn Lys Ile Arg Met Cys Val Gln Pro Pro Phe
            260                 265                 270

Phe Leu Phe Lys Gln Asn Asp Thr Ser Asn Asn Thr Asn Ile Leu Ser
        275                 280                 285

Asn Cys Gly Pro Leu Val Phe Leu Gly Ile Phe Glu Asp Asn Lys Ala
    290                 295                 300

Ala Ile Gln Asn Gly Ser Cys Thr Leu His Arg Thr Asn Ile Asn Arg
305                 310                 315                 320

Pro Asp Tyr Ser Gly Phe Tyr Gln Val Pro Ile Phe Tyr Ile Cys Thr
                325                 330                 335

Leu Thr Gly Phe Gln Ser Cys Asn Asn Gly Ser Ile Ile Ser Ile Ile
            340                 345                 350

Met Tyr Glu Ser Asn Asn Val Gln Tyr Leu Leu Cys Asn Thr Ser Asn
        355                 360                 365
```

-continued

```
Thr Asn Ser Thr Asn Asn Ala Asn Val Ser Cys Val Val Gln Ser Phe
    370                 375                 380

Gly Val Ile Gly Gln Ala His Val Ala Leu Pro Arg Lys Asn Lys Arg
385                 390                 395                 400

Leu Gln Ser Pro Lys Phe Ala His Tyr Asn Cys Thr Ile Asn Asn Lys
                405                 410                 415

Thr Glu Leu Arg Arg Trp Gln Leu Val Lys Thr Ser Gly Ile Thr Pro
            420                 425                 430

Leu Pro Ile Ser Ser Thr Ala Asn Thr Gly Leu Val Arg His Lys Arg
        435                 440                 445

Asp Phe Gly Ile Ser Ala Ile Ala Ala Ile Val Ala Ala Ser Ala
    450                 455                 460

Ile Ala Ala Ser Ala Thr Met Ser Tyr Ile Ala Leu Thr Glu Val Asn
465                 470                 475                 480

Lys Leu Asp Ser Val Gln Asn His Thr Phe Glu Val Glu Asn Asn Thr
                485                 490                 495

Ile Asn Asn Ile Glu Leu Thr Glu Glu Gln Ile His Ile Leu Tyr Ala
            500                 505                 510

Met Val Leu Gln Thr His Ala Asp Val Gln Leu Leu Lys Glu Gln Gln
        515                 520                 525

Lys Ile Glu Glu Thr Phe Asn Leu Ile Gly Cys Ile Glu Arg Ser His
    530                 535                 540

Thr Phe Cys His Thr Gly His Pro Trp Asn Glu Ser Trp Gly Gln Leu
545                 550                 555                 560

Asn Asp Ser Thr Gln Trp Asp Trp Val Asp Lys Met Glu Asn Leu
                565                 570                 575

Asn His Asp Ile Leu Thr Thr Leu His Thr Ala Arg Asn Asn Leu Glu
            580                 585                 590

Gln Ser Met Ile Thr Phe Asn Thr Pro Asp Ser Val Ala Gln Phe Gly
        595                 600                 605

Lys Asn Ile Trp Ser His Ile Ala Asn Trp Ile Pro Arg Leu Gly Ala
    610                 615                 620

Ser Ile Ile Lys Tyr Ile Val Leu Ile Leu Ile Tyr Val Leu Leu
625                 630                 635                 640

Thr Ser Ala Pro Lys Ile Leu Arg Gly Leu Leu Thr Thr Met Ser Gly
                645                 650                 655

Ala Gly Ser Ser Ala Ser Arg Tyr Leu Lys Lys Arg Tyr His His Lys
            660                 665                 670

His Ala Ser Arg Gly Asp Ile Trp Ala Gln Val Gln Tyr His Ala Tyr
        675                 680                 685

Leu Ala Asp Glu Thr His Gly Ser Gly Asp Lys Ser Asn Met Arg Lys
    690                 695                 700

Leu Ser Arg Asn Asn Trp Asn Gly Glu Ser Glu Tyr Asn Arg Arg
705                 710                 715                 720

Gln Lys Asn Trp Lys Lys Leu Leu Lys Arg Ser Gly Glu Asn Tyr Asn
                725                 730                 735

Thr His Glu Asp Asn Met Gly Thr Met Gly Arg Leu Val Thr Thr Ala
            740                 745                 750

Ala Glu Lys Lys Asn Val Gly Val Asn Pro His Gln Gly Ser Leu Thr
        755                 760                 765

Leu Glu Ile Gln Ser Lys Gly Gly Asn Ile Tyr Asp Cys Cys Ile Lys
    770                 775                 780
```

```
Ala Gln Glu Gly Thr Leu Ala Ile Pro Cys Cys Gly Phe Pro Leu Trp
785                 790                 795                 800

Pro Phe Trp Gly Leu Ile Ile Ile Leu Glu Arg Leu Leu Gly Tyr Gly
            805                 810                 815

Leu Arg Glu Ile Ala Lys Ile Ile Met Ile Leu Gly Lys Gly Leu Ser
        820                 825                 830

Ile Ile Ile Thr Gly Leu Arg Lys Leu Cys Asp Tyr Ile Gly Lys Met
            835                 840                 845

Leu Asn Pro Ala Thr Ser His Val Thr Met Pro Gln Tyr Asp Val
    850                 855                 860

<210> SEQ ID NO 6
<211> LENGTH: 862
<212> TYPE: PRT
<213> ORGANISM: Equine infectious anemia virus
<220> FEATURE:
<223> OTHER INFORMATION: Amino acid sequence of EIAV FDDV strain
      envelope protein

<400> SEQUENCE: 6

Met Val Ser Ile Ala Phe Tyr Gly Gly Ile Pro Gly Gly Ile Ser Thr
1               5                   10                  15

Pro Ile Thr Gln Gln Thr Glu Ser Thr Asp Thr Gln Lys Gly Asp His
            20                  25                  30

Met Val Tyr Gln Pro Tyr Cys Tyr Asn Asp Ser His Lys Glu Glu Met
        35                  40                  45

Ala Glu Ala Arg Asp Thr Arg Tyr Gln Glu Glu Met Asn Arg Lys Glu
    50                  55                  60

Asp Lys Glu Asp Lys Arg Arg Asn Asn Trp Trp Lys Ile Gly Met Phe
65                  70                  75                  80

Leu Leu Cys Leu Leu Gly Thr Thr Gly Gly Phe Leu Trp Trp Tyr Glu
                85                  90                  95

Arg Gln Gln His Ser Tyr Tyr Ile Gly Leu Val Thr Ile Gly Gly Arg
            100                 105                 110

Leu Asn Gly Ser Gly Met Thr Ser Ala Ile Glu Cys Trp Gly Ser Phe
        115                 120                 125

Pro Gly Cys Arg Ser Phe Thr Asn Tyr Phe Ser Tyr Asp Thr Asn Arg
    130                 135                 140

Thr Val Ser Thr Asp Asn Asn Thr Ala Thr Leu Leu Asp Ala Tyr Gln
145                 150                 155                 160

Arg Glu Ile Thr Asn Ile Tyr Arg Thr Ser Cys Val Asp Ser Asp His
                165                 170                 175

Cys Gln Lys Tyr Lys Cys Asn Gln Val Gln Leu Glu Lys Asn Ser Asn
            180                 185                 190

Asn Ile Ile Met Asn Asn Cys Ser Asn Ser Cys Glu Glu Phe Trp
        195                 200                 205

Gly Phe Ser Trp Leu Glu Cys Asn Gln Thr Glu Asn Ala Ile Thr Ile
    210                 215                 220

Leu Val Pro Glu Val Glu Met Gln Gln Ser Lys Asn Thr Trp Ile Pro
225                 230                 235                 240

Lys Gly Cys Asn Glu Thr Trp Ala Arg Val Lys His Cys Pro Met Asp
                245                 250                 255

Leu Leu Tyr Gly Ile Asn Arg Ile Arg Met Cys Val Gln Pro Pro Phe
            260                 265                 270

Phe Leu Phe Lys Gln Asp Asp Thr Ser Asn Asn Thr Gly Ile Leu Ser
        275                 280                 285
```

```
Asn Cys Gly Pro Leu Val Phe Leu Gly Ile Leu Glu Asp Asn Lys Ala
        290                 295                 300

Ala Ile Gln Asn Gly Ser Cys Thr Leu His Arg Thr Asn Ile Glu Arg
305                 310                 315                 320

Pro Asp Tyr Ser Gly Phe Tyr Gln Val Pro Ile Phe Tyr Ile Cys Asn
                325                 330                 335

Leu Thr Gly Leu Gln Ser Cys Asn Asn Gly Ser Ile Ile Ser Ile Ile
            340                 345                 350

Met Ser Glu Pro Asn Asn Val Gln Tyr Leu Leu Cys Asn Thr Ser Asn
        355                 360                 365

Thr Asn Ser Thr Ser Asn Ala Asn Val Ser Cys Val Val Gln Ser Phe
    370                 375                 380

Gly Val Ile Gly Gln Ala His Val Ala Leu Pro Arg Lys Asn Lys Arg
385                 390                 395                 400

Leu Gln Ser Pro Lys Phe Ala Gln Tyr Asn Cys Thr Ile Asn Asn Lys
                405                 410                 415

Thr Glu Leu Arg Gln Trp Gln Leu Val Lys Thr Ser Gly Ile Thr Pro
            420                 425                 430

Leu Pro Ile Ser Ser Thr Ala Asn Thr Gly Leu Val Arg His Lys Arg
        435                 440                 445

Asp Phe Gly Ile Ser Ala Ile Ile Ala Ala Ile Val Ala Ala Thr Ala
    450                 455                 460

Ile Ala Ala Ser Ala Thr Met Ser Tyr Ile Ala Leu Thr Glu Val Asn
465                 470                 475                 480

Lys Leu Asp Ser Val Gln Asn His Thr Phe Lys Val Glu Asn Asn Thr
                485                 490                 495

Ile Asn Ser Met Glu Leu Val Glu Gln Ile His Ile Leu Tyr Ala
            500                 505                 510

Met Val Leu Gln Thr His Ala Asp Val Gln Leu Leu Lys Glu Gln Gln
        515                 520                 525

Lys Ile Glu Glu Thr Phe Asn Leu Ile Gly Cys Ile Glu Arg Ser His
    530                 535                 540

Thr Phe Cys His Thr Gly His Pro Trp Asn Glu Ser Trp Gly Gln Leu
545                 550                 555                 560

Asn Asp Ser Thr Gln Trp Asp Asp Trp Val Asp Lys Met Glu Asn Leu
                565                 570                 575

Asn His Asp Ile Leu Thr Thr Leu His Thr Ala Arg Asn Asn Leu Glu
            580                 585                 590

Gln Ser Met Ile Thr Phe Asn Thr Pro Asp Ser Ile Ala Gln Phe Gly
        595                 600                 605

Lys Asn Ile Trp Ser His Val Ala Asn Trp Ile Pro Gly Leu Gly Ala
    610                 615                 620

Ser Ile Ile Lys Tyr Ile Val Leu Leu Leu Val Tyr Val Leu Leu
625                 630                 635                 640

Thr Ser Ala Pro Lys Ile Leu Arg Gly Leu Thr Thr Met Ser Gly
                645                 650                 655

Ala Gly Ser Ser Ala Ser Arg Tyr Leu Arg Lys Arg Tyr His His Arg
            660                 665                 670

His Ala Ser Arg Gly Asp Ile Trp Ala Gln Val Gln Tyr His Ala Tyr
        675                 680                 685

Leu Ala Asp Glu Thr His Gly Ser Gly Asp Lys Ser Asn Met Arg Lys
        690                 695                 700
```

```
Phe Ser Arg Asn Asn Asn Gly Glu Ser Glu Glu Tyr Asn Arg Arg Gln
705                 710                 715                 720

Lys Asn Trp Lys Arg Leu Ile Lys Arg Ser Gly Glu Asn Tyr Asn Thr
            725                 730                 735

His Glu Asp Asn Met Gly Thr Met Gly Arg Leu Val Thr Thr Ala Ala
        740                 745                 750

Glu Lys Lys Asn Val Gly Val Asn Pro His Gln Gly Ser Leu Asn Leu
    755                 760                 765

Glu Ile Pro Ser Glu Gly Asn Ile Tyr Asp Cys Cys Leu Lys Ala
    770                 775                 780

Gln Glu Gly Thr Leu Ala Ile Pro Cys Cys Gly Phe Pro Leu Trp Leu
785                 790                 795                 800

Leu Trp Gly Leu Ile Ile Ile Leu Gly Arg Leu Leu Gly Tyr Gly Leu
                805                 810                 815

Arg Gly Ile Ala Lys Ser Ile Met Ile Leu Gly Lys Gly Leu Asn Val
                820                 825                 830

Ile Ile Thr Gly Leu Arg Lys Leu Cys Asn Tyr Ile Gly Lys Met Leu
                835                 840                 845

Asn Pro Ala Thr Ser His Val Thr Met Pro Gln Tyr Asp Val
    850                 855                 860

<210> SEQ ID NO 7
<211> LENGTH: 44
<212> TYPE: DNA
<213> ORGANISM: Artificial sequence
<220> FEATURE:
<223> OTHER INFORMATION: gp145 upstream primer

<400> SEQUENCE: 7
gctctagaga tatcgacacc atggacaggg ccaagctgct gctg        44

<210> SEQ ID NO 8
<211> LENGTH: 41
<212> TYPE: DNA
<213> ORGANISM: Artificial sequence
<220> FEATURE:
<223> OTHER INFORMATION: gp145 downstream primer

<400> SEQUENCE: 8
gtgaacaggg tgaggcaggg ctactgagga tccgtcgacc g           41

<210> SEQ ID NO 9
<211> LENGTH: 25
<212> TYPE: DNA
<213> ORGANISM: Artificial sequence
<220> FEATURE:
<223> OTHER INFORMATION: 145M1R position upstream primer

<400> SEQUENCE: 9
accaccgagt tctgcgccag cgacg                             25

<210> SEQ ID NO 10
<211> LENGTH: 36
<212> TYPE: DNA
<213> ORGANISM: Artificial sequence
<220> FEATURE:
<223> OTHER INFORMATION: 145M1R position downstream primer

<400> SEQUENCE: 10
cgcagaactc ggtggtggtg gcgcccttcc acacgg                 36
```

```
<210> SEQ ID NO 11
<211> LENGTH: 24
<212> TYPE: DNA
<213> ORGANISM: Artificial sequence
<220> FEATURE:
<223> OTHER INFORMATION: 145M2R position upstream primer

<400> SEQUENCE: 11
aaccaggaca cctaccacga gacc                                              24

<210> SEQ ID NO 12
<211> LENGTH: 39
<212> TYPE: DNA
<213> ORGANISM: Artificial sequence
<220> FEATURE:
<223> OTHER INFORMATION: 145M2R position downstream primer

<400> SEQUENCE: 12
ctcctcgtgg taggtgtcct ggttgctgct cacgttcct                              39

<210> SEQ ID NO 13
<211> LENGTH: 26
<212> TYPE: DNA
<213> ORGANISM: Artificial sequence
<220> FEATURE:
<223> OTHER INFORMATION: 145M3R position upstream primer

<400> SEQUENCE: 13
accgtggtgg aggacaggaa gcagac                                            26

<210> SEQ ID NO 14
<211> LENGTH: 30
<212> TYPE: DNA
<213> ORGANISM: Artificial sequence
<220> FEATURE:
<223> OTHER INFORMATION: 145M3R position downstream primer

<400> SEQUENCE: 14
ttcctgtcct ccaccacggt ggtggcgttg                                        30

<210> SEQ ID NO 15
<211> LENGTH: 37
<212> TYPE: DNA
<213> ORGANISM: Artificial sequence
<220> FEATURE:
<223> OTHER INFORMATION: 145M4R position upstream primer

<400> SEQUENCE: 15
ctacgagaag aacagccagg agtactacag gctgatc                                37

<210> SEQ ID NO 16
<211> LENGTH: 31
<212> TYPE: DNA
<213> ORGANISM: Artificial sequence
<220> FEATURE:
<223> OTHER INFORMATION: 145M4R position downstream primer

<400> SEQUENCE: 16
cctggctgtt cttctcgtag ttcttcttgg t                                      31

<210> SEQ ID NO 17
<211> LENGTH: 40
<212> TYPE: DNA
<213> ORGANISM: Artificial sequence
<220> FEATURE:
<223> OTHER INFORMATION: 145M5R position upstream primer
```

```
<400> SEQUENCE: 17
atcttcaacc gcacccagcc ctgctacaac gtgagcaccg                            40

<210> SEQ ID NO 18
<211> LENGTH: 36
<212> TYPE: DNA
<213> ORGANISM: Artificial sequence
<220> FEATURE:
<223> OTHER INFORMATION: 145M5R position downstream primer

<400> SEQUENCE: 18
gttgtagcag ggctgggtgc ggttgaagat cttgtc                               36
```

ANTI-HIV VACCINE CONSTRUCTED BASED ON AMINO ACID MUTATIONS IN ATTENUATED LIVE EIAV VACCINE

CROSS-REFERENCE TO RELATED APPLICATIONS

This application is a national stage filing of PCT/CN2009/072017, filed on May 27, 2009, which claims priority to Chinese Application No. 200810097471.3, filed on May 27, 2008, both of which are incorporated by reference in their entirety for all purposes.

This invention relates to the filed of immunology, and in particular relates to an antigenic polypeptide derived from HIV (Human Immunodeficiency Virus) envelope protein, a DNA construct and a recombinant viral vector comprising a polynucleotide that encodes said polypeptide, an antibody against said antigenic polypeptide, and the use thereof for preventing or treating HIV infection.

BACKGROUND OF THE INVENTION

Human immunodeficiency virus (HIV) is the pathogen that causes the acquired immunodeficiency syndrome (AIDS). According to WHO, globally, there were an estimated 33 million people living with HIV in 2007. The annual number of new HIV infections was 2.5 million last year, or an increase of about 6800 daily. Regionally, sub-Saharan Africa and under-developed Asia countries are still home to most of the people living with HIV.

HIV is one member of Lentivirus genus of the Retroviridae family. Up to now, the epidemic thereof can only be retarded but not terminated; effective antiretroviral therapy can only slow down the development of the disease, while cannot completely eliminate the virus. Moreover, it remains financially unaffordable for those who reside in the developing countries. It is thus widely believed that an effective vaccine is the only solution to restrain the global HIV-1 epidemic.

Anti-HIV candidate vaccines currently under investigation include: attenuated viable vaccines, deactivated vaccines, DNA vaccines, viable vector vaccines, subunit vaccines and protein vaccines. With respect to the development history of anti-HIV vaccines, they can be divided into 4 generations. The first generation (1980s) of HIV candidate vaccines was mainly based on protein subunit concept. These candidates are capable of inducing neutralizing antibodies, but not cytotoxic T lymphocytes. The second generation (1990s) vaccine is based on the concept of recombinant vectors, especially using virus vectors followed by boosting with subunit recombinant vaccines. This concept is theoretically very attractive because preliminary data suggest that these vaccines induce both humoral and cell-mediated immunity. However, these vaccines have failed to protect vaccines from HIV infection. The third generation (2000-2005) of HIV candidate vaccines was based on the feature of different vaccine vectors and strategy to proceed carefully to expanded phase II and phase III trials to assess the protective efficacy of these candidate vaccines in humans. The new concept is based on inducing potent immune response by HIV conserved epitopes.

The HIV-1 envelope glycoprotein is the primary target for neutralization, and great efforts have been made to enhance the immunogenicity of Env in AIDS vaccine design. However, the Env glycoproteins frequently change their sequence in response to selective pressure exerted by the immune system, thus presenting the host with ever new antigens (Parren P W, et al. The neutralizing antibody response to HIV-1: viral evasion and escape from humoral immunity. AIDS 1999.13 (Suppl A):S137-162). Furthermore, the trimeric Env structure shields important domains of the Env core, making them inaccessible to antibody-mediated neutralization. Conformational Env re-orientation upon CD4 receptor binding transiently uncovers neutralization-sensitive regions for coreceptor binding until the viral envelope fuses with the host cell membrane In addition, heavy glycosylation on the outside of gp120 hides much of the protein core from antibody attack (Kwong P D, et al. HIV-1 evades antibody-mediated neutralization through conformational masking of receptor-binding sites. Nature 2002. 420:678-682). In all, the HIV Env protein poses a great challenge for generating broad reactive neutralizing antibodies. To induce a potent and cross-reactive neutralizing antibody, an effective envelope immunogen must be modified for HIV vaccine Because of the lack of suitable animal model for HIV in nature, and human cannot be used for challenging test, people then turn to other six animal Lentivirus that belong to the same genus with HIV for relevant researches. Wherein, equine infectious anemia virus (EIAV) belongs to the same genus with HIV, and they both have same genome structures, replication modes, and similar protein categories and functions. It has been found that the V1, V2 regions of HIV-1 have a certain corresponding relations with the V3, V4 regions of EIAV (Hotzel I. Conservation of the human immunodeficiency virus type 1 gp120 V1/V2 stem/loop structure in the equine infectious anemia virus (EIAV) gp90. AIDS Res Hum Retroviruses, 2003, 19:923-924; and Huiguang Li, et al. A Conservative Domain Shared by HIV gp120 and EIAV gp90: Implications for HIV Vaccine Design. AIDS Res Hum Retroviruses, 2005, 21:1057-1059).

But due to the clear differences in the underlying mechanisms of pathogenesis of the two viruses, and which is different with HIV, the primary investigation process of attenuated EIAV vial vaccine is attenuation rather than the process of increasing immunogenicity. Hence, this alteration approach is all along despised by researchers in HIV vaccine development.

Based on the sequence analysis of the EIAV virulent strain and vaccine strain, and also based on the characteristic amino acid mutations of attenuated EIAV vial vaccine, the inventor utilized the approach of structurally and functionally corresponding positions to perform alterations for corresponding amino acid positions in HIV-1 envelope protein. Surprisingly, the altered antigenic polypeptide of HIV-1 envelope protein and vaccines constructed based on the polypeptide can induce the production of anti-HIV neutralizing antibodies with high tier, broad spectrum and persistence.

SUMMARY OF THE INVENTION

In one aspect, the present invention provides an antigenic polypeptide or a fragment thereof derived from HIV-1 envelope protein, wherein the polypeptide or fragment comprises an amino acid sequence containing a mutation selected from the group consisting of: substitution of the leucine residue at a position corresponding to position 52 in SEQ ID NO:1 by a glutamic acid or an aspartic acid residue; deletion of the serine residue at a position corresponding to position 138 in SEQ ID NO:1; substitution of the asparagine residue at a position corresponding to position 139 in SEQ ID NO:1 by a glutamine residue; substitution of the arginine residue at a position corresponding to position 166 in SEQ ID NO:1 by a glutamic acid or an aspartic acid residue; substitution of the serine residue at a position corresponding to position 184 in SEQ ID NO:1 by a glutamic acid or an aspartic acid residue; substitution of the glutamic acid residue at a position corresponding to position 185 in SEQ ID NO:1 by a lysine, an arginine or a histidine residue; substitution of the serine residue at a position corresponding to position 188 in SEQ ID NO:1 by a glutamine or an asparagine residue; substitution of the glycine residue at a position corresponding to position 235 in SEQ ID NO:1 by an arginine, a lysine or a histidine residue; substitution of the glycine residue at a position corresponding to position 237 in SEQ ID NO:1 by a glutamine or an asparagine residue; substitution of the histidine residue at a position corresponding to position 240 in SEQ ID NO:1 by a tyrosine residue; and any combination thereof.

In a preferred embodiment, the amino acid sequence of the polypeptide or fragment according to the present invention contains at least the mutation of substitution of the leucine residue at the position corresponding to position 52 in SEQ ID NO:1 by a glutamic acid or an aspartic acid residue. In a more preferred embodiment the amino acid sequence of the polypeptide or fragment according to the present invention contains the above mentioned substitution of the leucine residue at the position corresponding to position 52 in SEQ ID NO:1 by a glutamic acid or an aspartic acid residue; the deletion of the serine residue at the position corresponding to position 138 in SEQ ID NO:1; and the substitution of the asparagine residue at the position corresponding to position 139 in SEQ ID NO:1 by a glutamine residue. In an even more preferred embodiment, the amino acid sequence of the polypeptide or fragment according to the present invention contains the above mentioned mutations at positions corresponding to all the 10 positions in SEQ ID NO:1.

HIV-1 envelope proteins that can be used in this invention comprise gp120, gp128, gp140, gp140TM, gp145, gp150, gp160, and an equivalent thereof originated from various HIV-1 strains. For example, the HIV-1 envelope protein can be the gp145 of HIV-1 CN54 having the amino acid sequence of SEQ ID NO:2.

In a specific embodiment, the invention provides an antigenic polypeptide or a fragment thereof derived from HIV-1 envelope protein, wherein the polypeptide or fragment thereof comprises an amino acid sequence derived from SEQ ID NO:2 by introducing a mutation into SEQ ID NO:2, wherein the mutation is selected from the group consisting of: substitution of the leucine residue at position 42 by a glutamic acid residue; deletion of the serine residue at position 128; substitution of the asparagine residue at position 129 by a glutamine residue; substitution of the arginine residue at position 155 by a glutamic acid residue; substitution of the serine residue at position 179 by a glutamic acid residue; substitution of the glutamic acid residue at position 180 by a lysine residue; substitution of the serine residue at position 183 by a glutamine residue; substitution of the glycine residue at position 230 by an arginine residue; substitution of the glycine residue at position 232 by a glutamine residue; substitution of the histidine residue at position 235 by a tyrosine residue; and any combination thereof.

In a preferred embodiment, the polypeptide or fragment according to the present invention comprises an amino acid sequence derived from SEQ ID NO:2, wherein the amino acid sequence contains at least the mutation of substitution of the leucine residue at position 42 by a glutamic acid residue. In a more preferred embodiment, the amino acid sequence derived from SEQ ID NO:2 contains at least the following mutations: substitution of the leucine residue at position 42 by a glutamic acid residue; deletion of the serine residue at position 128; and substitution of the asparagine residue at position 129 by a glutamine residue. In an even more preferred embodiment, the amino acid sequence derived from SEQ ID NO:2 contains the above mentioned mutations at all the 10 positions.

An antigenic polypeptide or fragment according to the invention can further comprise substitution, deletion or addition of one or more amino acids, and the polypeptide or fragment thereof is capable of inducing protective immune response. Moreover, the antigenic polypeptide or fragment thereof according to the invention can also contain additional modifications, e.g. deletion or addition of a glycosylation site, deletion or rearrangement of the loop region, deletion of the CFI region, and combinations thereof.

In another aspect, the invention provides a polypeptide vaccine comprising the above described antigenic polypeptide or fragment thereof according to the present invention together with a pharmaceutical acceptable adjuvant and/or carrier.

In another aspect, the invention also provides an antibody which is capable of specifically binding to the above described antigenic polypeptide or fragment thereof according to the present invention, and the antibody has a broader and higher neutralization activity to HIV-1 virus when compared to an antibody produced by induction with a wild-type envelope protein of HIV-1. Antibodies of the invention comprise polyclonal antibodies, monoclonal antibodies or antigen binding fragments thereof.

In another aspect, the invention provides an isolated polynucleotide comprising a nucleotide sequence that encodes the above described antigenic polypeptide or fragment thereof according to the invention.

The invention also provides a DNA construct comprising a polynucleotide operably linked to a promoter, wherein the polynucleotide comprises a nucleotide sequence that encodes the above described antigenic polypeptide or fragment thereof according to the invention. The present invention also provides a DNA vaccine comprising the above mentioned DNA construct together with a pharmaceutical acceptable adjuvant.

The invention also provides a recombinant viral vector vanccine, which comprises a recombinant viral vector carrying a polynucleotide together with a pharmaceutical acceptable adjuvant, wherein the polynucleotide comprises a nucleotide sequence that encodes the above described antigenic polypeptide or fragment thereof according to the invention. Preferably, the recombinant viral vector is a replicative viral vector, e.g. a replicative recombinant vaccinia vector such as a recombinant vaccinia Tian Tan strain.

Additionally, the invention also provides a recombinant bacterial vector vaccine, which comprises a recombinant bacterial vector carrying a polynucleotide together with a pharmaceutical acceptable adjuvant, wherein the polynucleotide comprises a nucleotide sequence that encodes the above described antigenic polypeptide or fragment thereof according to the invention.

In other aspect, the invention also provides a method for preventing or treating HIV-1 virus infection comprising a step of administering the polypeptide vaccine and/or the DNA vaccine and/or the recombinant viral vector vaccine and/or the recombinant bacterial vector vaccine of the invention to a subject in need thereof, or administering the antibody of the invention to a subject in need thereof.

Figure 1:
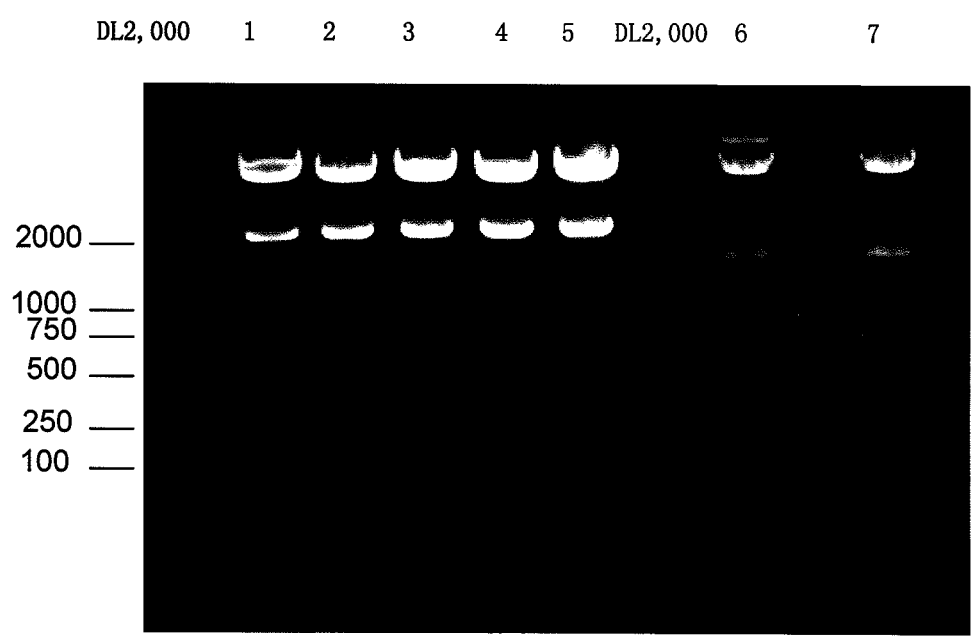
FIG. 1: The restriction analysis results of 7 DNA vaccines: Lane 1 is the restriction analysis result of pDRVISV145M1R; lane 2 is the restriction analysis result of pDRVISV145M2R; lane 3 is the restriction analysis result of pDRVISV145M3; lane 4 is the restriction analysis result of pDRVISV145M4R; lane 5 is the restriction analysis result of pDRVISV145M5R; lane 6 is the restriction analysis result of pDRVISV1452M; lane 7 is the restriction analysis result of pDRVISV1455M. As shown in this figure, the size of each vaccine vector gene is 5 Kb, and the size of the inserted target gene is 2.1 Kb.
Figure 2:
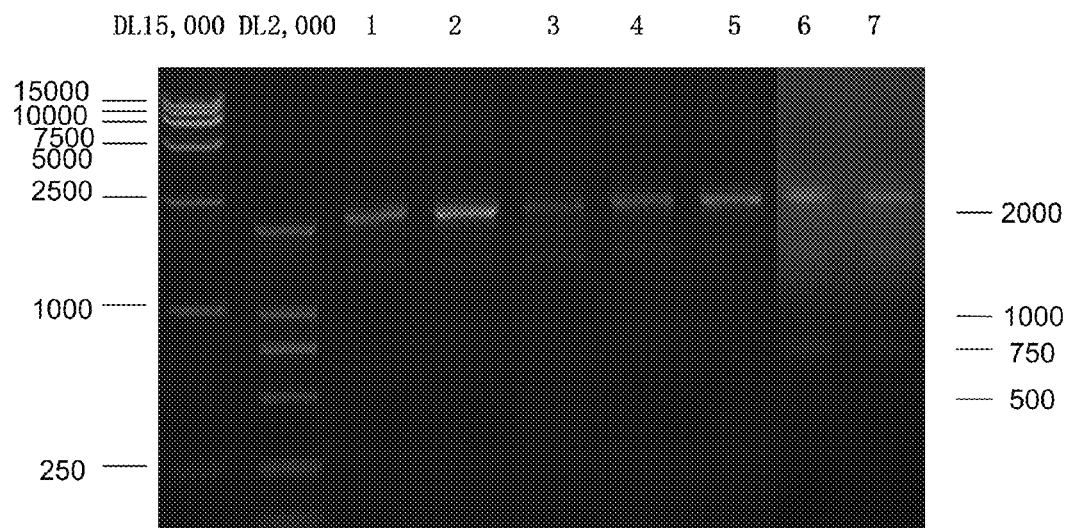
FIG. 2: Identification of 7 DNA vaccines by PCR.

Lane 1 is the PCR product of pDRVISV145M1R; lane 2 is the PCR product of pDRVISV145M2; lane 3 is the PCR product of pDRVISV145M3R; lane 4 is the PCR product of pDRVISV145M4R; lane 5 is the PCR product of pDRVISV145M5R; lane 6 is the PCR product of pDRVISV1452M; lane 7 is the PCR product of pDRVISV1455M. As shown in this figure, the size of each inserted target gene is 2.1 Kb.

Figure 3:
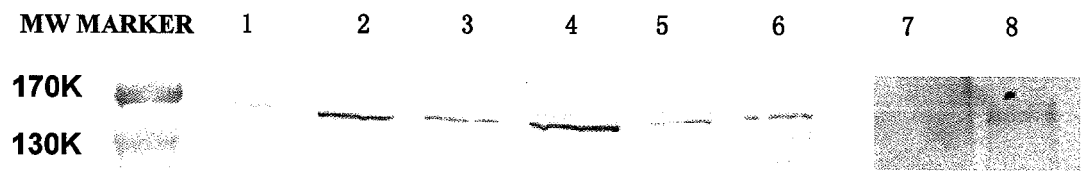

FIG. 3: The immunoblot analysis of each DNA vaccines:

Lane 1 is the expression result of pDRVISV145M1R; lane 2 is the expression result of pDRVISV145M2R; lane 3 is the expression result of pDRVISV145M3R; lane 4 is the expression result of pDRVISV145M4R; lane 5 is the expression result of pDRVISV145M5; lane 6 is the expression result of pDRVISV1452M; lane 7 is negative control; lane 8 is the expression result of pDRVISV1455M. As shown in this figure, each inserted target gene can be correctly expressed.

Figure 4:
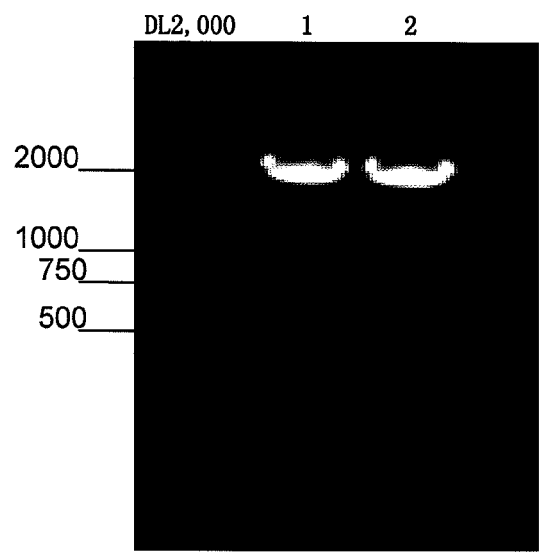

FIG. 4: Identification of recombinant vaccinia vectors by PCR:

Lane 1 is the PCR result of rTV145 PCR; lane 2 is the PCR result of rTV1455M PCR. As shown in this figure, each inserted target gene is at the correct size of 2.1 Kb.

Figure 5:
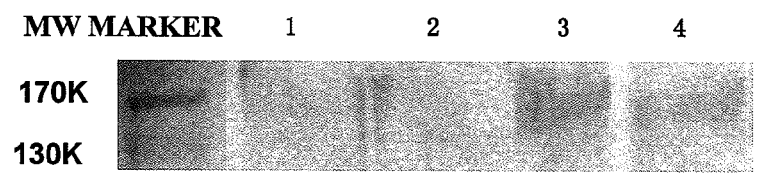

FIG. 5: The immunoblot analysis of the products expressed by recombinant vaccinia vectors:

Lane 1 is the cellular expression product of Chicken Embryo Fibroblasts (CEF), serving as a negative control; lane 2 is the expression result of wild-type vaccinia Tian Tan strain in CEF, serving as a negative control; lane 3 is the expression result of rTV145 in CEF; lane 4 is the expression result of rTV1455M in CEF. As shown in this figure, the size for the expression products of target genes are 145 KD, indicating that the inserted target genes can be correctly expressed.

Figure 6:
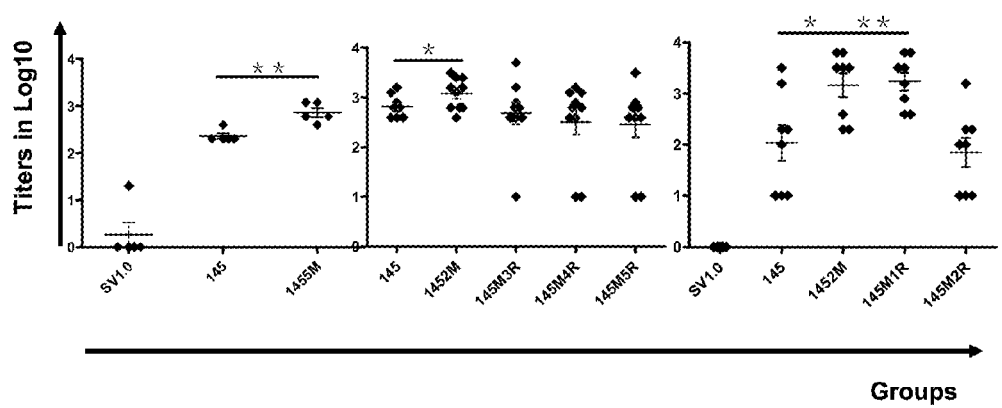

FIG. 6: ELISA assay of the titers of specifically binding antibodies:

The average titer of specifically binding antibodies stimulated by antigen 1455M is much higher than that stimulated by unaltered antigen gp145; the antibody titer thereof is increased for more than 3.5 fold (p=0.0020) (* means the p value is less than 0.05, and there is statistically significant difference; **means the p value is less than 0.005, and there is extremely statistically significant difference). The average titer of specifically binding antibodies stimulated by 1455M can reach 2400, the highest titer can reach 9600, which is significantly higher than that of unaltered gp145 (p=0.0177). The reaction intensity of antibodies induced by 145M1R is also significantly higher than that of gp145 (p=0.0177).

Figure 7:
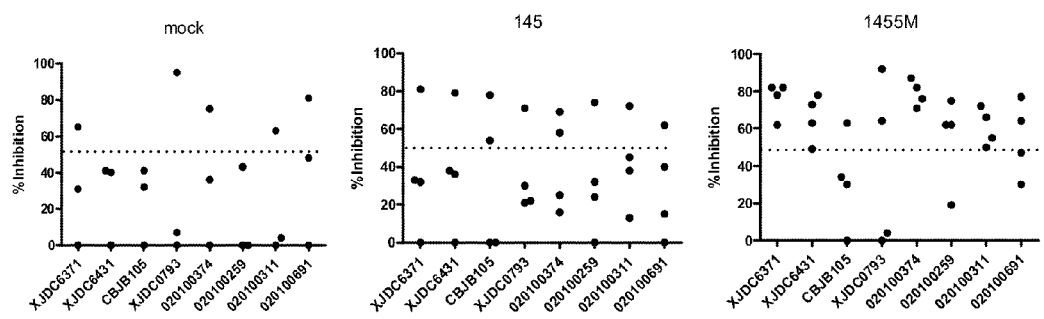

FIG. 7: Dectection of the neutralization antibody activity of guinea pig sera (1:10 diluted) sampled at the 14$^{th}$ week:

The antibodies induced in gp145 immunization group show limited neutralization activity, about ¼ of the guinea pigs display the ability to neutralize all the 8 clinical isolates; while in 1455M immunization group, at least ¾ of the guinea pigs display neutralization activity to all isolates.

Figure 8:
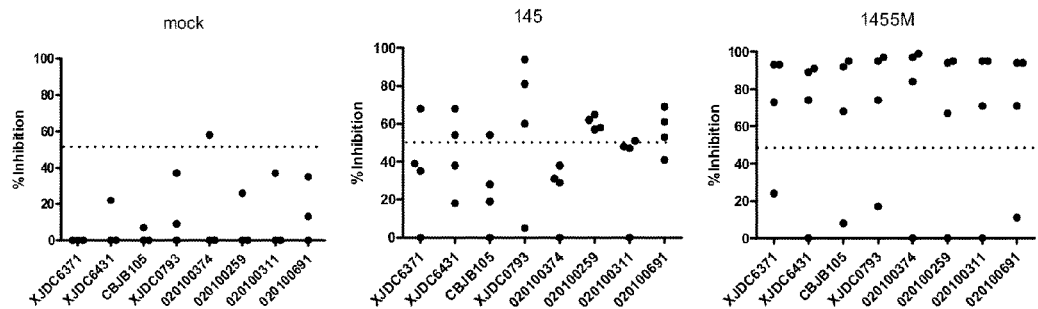

FIG. 8: Dectection of the neutralization antibody activity of guinea pig sera (1:10 diluted) sampled at the 16$^{th}$ week:

The antibody spectrum induced in gp145 immunization group is narrow, half of the B' sub-type virus are not neutralized; while ¾ of the serum samples from 1455M immunization group guinea pigs shows neutralization activity to all isolates.

Figure 9:
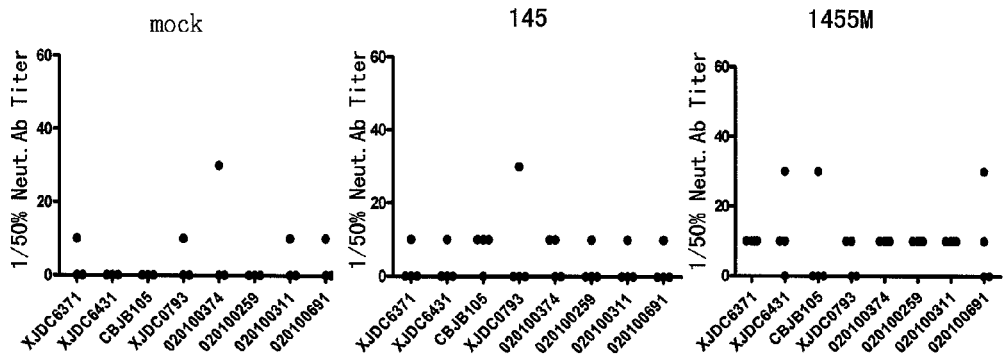

FIG. 9: Dectection of the neutralization antibody titer of guinea pig sera sampled at the 14$^{th}$ week:

Only few guinea pig sera in gp145 immunization group show neutralization activity at 1:10 dilution; while most of the guinea pigs in 1455M immunization group show neutralization activity with titer higher than 1:10.

Figure 10:
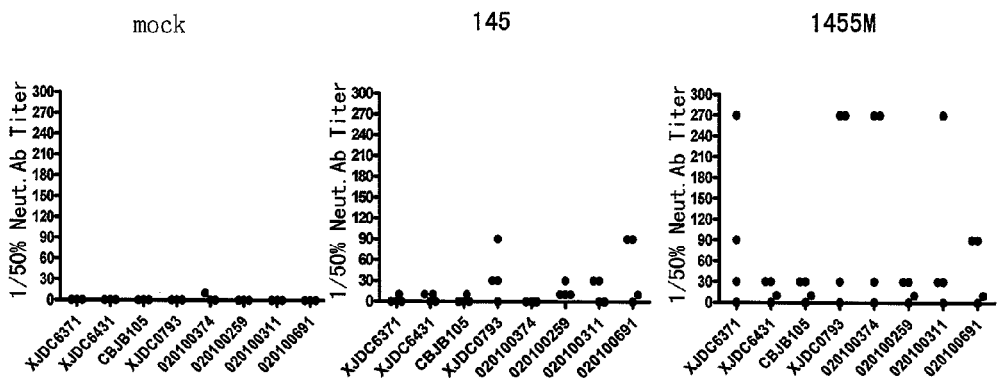

FIG. 10: Dectection of the neutralization antibody titer of guinea pig sera sampled at the 16$^{th}$ week:

Most of the guinea pig sera in 1455M immunization group can completely neutraliz all the virus, with the highest titer up to 1:270; while only a few guinea pig sera in gp145 immunization group have an antibody titer higher than 1:10.

DETAILED DESCRIPTION

Based on the characteristic amino acid mutations of the attenuated live EIAV vaccine, the inventors modified the amino acids in corresponding structural and functional positions of HIV-1 envelope protein.

Both EIAV and HIV are members of Lentivirus, they have the same genome structures and replication modes, and proteins of similar categories and functions. Therefore, the study on attenuated live EIAV vaccine may provide instructions for the modifications of HIV-1 envelope antigen. But there also exist clear differences in their underlying mechanisms of pathogenesis. At the same time, the primary purpose for the development of attenuated live EIAV vaccine is the attenuation rather than increasing immunogenicity. Hence, this modification approach has not been considered as promising by researchers in HIV vaccine development.

Up to now, the attenuated live EIAV vaccine developed in China is the only widely used lentiviral vaccine. Since the initial national application in 1979, more than 60 millions of Equus animals have been immunized, controlling the epidemics of the disease. In respect to safety, the vaccine also has been successfully tested for several decades by in-the-field application. EIAV vaccine is attenuated live vaccine developed by Harbin Veterinary Research Institute of Chinese Academy of Agricultural Sciences in 1970s. The vaccine was developed with traditional methods, the nomenclature in the development and passaging process of the vaccine will be briefly described: the wild-type viral strain was isolated from an infected horse in Liaoning Province, referred to as EIAV LN strain (LN). The LN strain was fisrt passaged in donkey for 100 generations to obtain donkey virulent strain (D510), D510 was then passaged on donkey leucocyte for 121 generations to obtain the attenuated live vaccine strain (referred to as donkey leucocyte virus, DLV), which was finally adaptively passaged on fetal donkey dermal cell for 10 generations to obtain fetal donkey dermal cell vaccine strain (FDDV) (Chinese Patent Nos.: 99105852.6 and 99127532.2, U.S. Pat. No. 6,987,020B1).

Through sequencing the full length envelope proteins of attenuated live EIAV vaccine strains (DLV (SEQ ID NO:5), FDDV (SEQ ID NO:6)) and virulent stains (LN (SEQ ID NO:3), D510 (SEQ ID NO:4)), the inventors found that there are 10 characteristic amino acid mutations on the envelope protein of the attenuated live EIAV vaccine, as shown in Table 1.

TABLE 1

10 characteristic amino acid mutations and their positions
on the envelope protein of attenuated live EIAV vaccine

| amino acid position number in EIAV envelope protein | 46 | 97 | 99 | 102 | 188 | 189 | 192 | 235 | 236 | 320 |
|---|---|---|---|---|---|---|---|---|---|---|
| amino acid residues in EIAV virulent stains | A | G | K (H) | H | K | E | S | D | N | K |
| amino acid residues in attenuated Live EIAV vaccine stains | E | R | Q | Y | E | K | N | — | K | N (E) |

— denotes deletion of amino acid residue

Based on primary amino acid sequence, structural arrangement in loop region, the formation of disulfide linkages, structure of conservative amino acids, known functional sites as well as number and arrangement of glycosylation sites etc., the inventors performed modifications on the HIV-1 envelope protein according to the characteristic amino acid mutations of the attenuated Live EIAV vaccine.

TABLE 2

Characteristics amino acid mutations of EIAV envelope protien
and the mutations and positions on HIV envelope protien after modification.

| positions of mutations on EIAV envelope protein. | | | positions of mutations on HIV envelope protein (3) | | |
|---|---|---|---|---|---|
| virulent stains | attenuated live vaccine stains | domain | before modification | after modification | domain |
| $^{43}$SHKAEMAE$^{50}$ | $^{43}$SHKEEMAE$^{50}$ (1) | C1 region | $^{37}$GATTLFCA$^{45}$ | $^{37}$GATTTEFCA$^{45}$ | C1 region |
| $^{235}$SDNNTW$^{240}$ | $^{235}$S-KNTW$^{240}$ (2) | V4 region | $^{125}$SSNSNDTY$^{132}$ | $^{125}$SSN-QDTY$^{132}$ | V1 region |
| $^{317}$TNIKRPDY$^{324}$ | $^{317}$TNIERPDY$^{324}$ | V5 region | $^{152}$TVVRDRK$^{158}$ | $^{152}$TVVEDRK$^{158}$ | V2 region |
| $^{188}$LKENSSN$^{194}$ | $^{188}$LEKNSNN$^{194}$ | V3 region | $^{178}$YSENSSE$^{184}$ | $^{178}$yEKNSQE$^{184}$ | V2 region |
| $^{94}$WYEGQKHSHYI$^{104}$ | $^{94}$WYERQQHSYYI$^{104}$ | V1 region | $^{227}$IFNGTGPCHNV$^{237}$ | $^{227}$IFNETQPCYNV$^{237}$ | C2 region |

1 positions with bold underline are mutation positions;
2 - denotes the deletion of the amino acid;
3 The amino acid positions og HIV envelope protien are corresponding to the positions on gp145 amino acid sequence if HIV-1 CN54 (SEQ ID NO: 2).

Accordingly, in one aspect, the present invention provides an antigenic polypeptide or a fragment thereof derived from HIV-1 envelope protein, wherein the polypeptide or fragment comprises an amino acid sequence containing a mutation selected from the group consisting of: substitution of the leucine residue at a position corresponding to position 52 (in C1 region) in SEQ ID NO:1 by a glutamic acid or an aspartic acid residue; deletion of the serine residue at a position corresponding to position 138 (in V1 region) in SEQ ID NO:1; substitution of the asparagine residue at a position corresponding to position 139 (in V1 region) in SEQ ID NO:1 by a glutamine residue; substitution of the arginine residue at a position corresponding to position 166 (in V2 region) in SEQ ID NO:1 by a glutamic acid or an aspartic acid residue; substitution of the serine residue at a position corresponding to position 184 (in V2 region) in SEQ ID NO:1 by a glutamic acid or an aspartic acid residue; substitution of the glutamic acid residue at a position corresponding to position 185 (in V2 region) in SEQ ID NO:1 by a lysine, an arginine or a histidine residue; substitution of the serine residue at a position corresponding to position 188 (in V2 region) in SEQ ID NO:1 by a glutamine or an asparagine residue; substitution of the glycine residue at a position corresponding to position 235 (in C2 region) in SEQ ID NO:1 by an arginine, a lysine or a histidine residue; substitution of the glycine residue at a position corresponding to position 237 (in C2 region) in SEQ ID NO:1 by a glutamine or an asparagine residue; substitution of the histidine residue at a position corresponding to position 240 (in C2 region) in SEQ ID NO:1 by a tyrosine residue; and any combination thereof.

The term "polypeptide" as used herein also includes protein. The term "fragment of polypeptide" means a fragment of the polypeptide with immunogenicity and/or antigenicity.

In a preferred embodiment, the amino acid sequence of the polypeptide or fragment according to the present invention contains at least the mutation of substitution of the leucine residue at the position corresponding to position 52 in SEQ ID NO:1 by a glutamic acid or an aspartic acid residue. In a more preferred embodiment, the amino acid sequence of the polypeptide or fragment according to the present invention contains the above mentioned substitution of the leucine residue at the position corresponding to position 52 in SEQ ID NO:1 by a glutamic acid or an aspartic acid residue; the deletion of the serine residue at the position corresponding to position 138 in SEQ ID NO:1; and the substitution of the asparagine residue at the position corresponding to position 139 in SEQ ID NO:1 by a glutamine residue. In an even more preferred embodiment, the amino acid sequence of the polypeptide or fragment according to the present invention contains the above mentioned mutations at positions corresponding to all the 10 positions in SEQ ID NO:1.

In another preferred embodiment, the amino acid sequence of the polypeptide or fragment according to the invention contains a mutation selected from the group consisting of: substitution of the leucine residue at a position corresponding to position 52 in SEQ ID NO:1 by a glutamic acid or an aspartic acid residue, deletion of the serine residue at a position corresponding to position 138 in SEQ ID NO:1, substitution of the asparagine residue at a position corresponding to position 139 in SEQ ID NO:1 by a glutamine residue, substitution of the arginine residue at a position corresponding to position 166 in SEQ ID NO:1 by a glutamic acid or an aspartic acid residue, substitution of the serine residue at a position corresponding to position 184 in SEQ ID NO:1 by a glutamic acid or an aspartic acid residue, substitution of the glutamic acid residue at a position corresponding to position 185 in SEQ ID NO:1 by a lysine, an arginine or a histidine residue, substitution of the serine residue at a position corresponding to position 188 in SEQ ID NO:1 by a glutamine or an asparagine residue, and any combinations thereof; and optionally comprising: substitution of the glycine residue at a position corresponding to position 235 in SEQ ID NO:1 by an arginine, a lysine or a histidine residue; substitution of the glycine residue at a position corresponding to position 237 in SEQ ID NO:1 by a glutamine or an asparagine residue, substitution of the histidine residue at a position corresponding to position 240 in SEQ ID NO:1 by a tyrosine residue, or combinations thereof.

The above mentioned positions are defined according to the gp160 amino acid sequence (SEQ ID NO:1) of HIV-1 international standard strain HXB2 (GenBank Accession Number K03455). A person skilled in the art can understand that, for envelope proteins from other HIV-1 strains, the corresponding positions to be mutated on these proteins can be determined according to their sequence alignments with SEQ ID NO:1. For example, using the gp160 amino acid sequence of HIV-1 international standard strain HXB2 as a reference sequence, the corresponding positions of above mentioned mutations can then be determined for gp160 envelope proteins from different HIV-1 strains, and thereby the modifications can be performed on these proteins. The envelope proteins that can be used in this invention include the typical gp120, gp128, gp140, gp140™, gp145, gp150, gp160, and an equivalent thereof (Bimal K. et al. Modifications of the Human Immunodeficiency Virus Envelope Glycoprotein Enhance Immunogenicity for Genetic Immunization JOURNAL OF VIROLOGY, June 2002, p. 5357-5368). A person skilled in the art can understand that, for the above mentioned different forms of HIV-1 envelope proteins, one can also use a similar approach to introduce the above described amino acid mutations into these proteins.

In a specific embodiment, the envelope protein used in this invention is HIV-1 CN54 envelope protein gp145 (Genbank Accession Number AX149771), which has an amino acid sequence as shown in SEQ ID NO:2.

Accordingly, the invention provides an antigenic polypeptide or a fragment thereof derived from HIV-1 envelope protein, wherein the polypeptide or fragment thereof comprises an amino acid sequence derived from SEQ ID NO:2 by introducing a mutation into SEQ ID NO:2, wherein the mutation is selected from the group consisting of: substitution of the leucine residue at position 42 (in C1 region) by a glutamic acid residue; deletion of the serine residue at position 128 (in V1 region); substitution of the asparagine residue at position 129 (in V1 region) by a glutamine residue; substitution of the arginine residue at position 155 (in V2 region) by a glutamic acid residue; substitution of the serine residue at position 179 (in V2 region) by a glutamic acid residue; substitution of the glutamic acid residue at position 180 (in V2 region) by a lysine residue; substitution of the serine residue at position 183 (in V2 region) by a glutamine residue; substitution of the glycine residue at position 230 (in C2 region) by an arginine residue; substitution of the glycine residue at position 232 (in C2 region) by a glutamine residue; substitution of the histidine residue at position 235 (in C2 region) by a tyrosine residue; and any combination thereof.

In a preferred embodiment, the polypeptide or fragment according to the present invention comprises an amino acid sequence derived from SEQ ID NO:2, wherein the amino acid sequence contains at least the mutation of substitution of the leucine residue at position 42 by a glutamic acid residue. In a more preferred embodiment, the amino acid sequence derived from SEQ ID NO:2 contains at least the following mutations: substitution of the leucine residue at position 42 by a glutamic acid residue; deletion of the serine residue at position 128; and substitution of the asparagine residue at position 129 by a glutamine residue. In an even more preferred embodiment, the amino acid sequence derived from SEQ ID NO:2 contains the above mentioned mutations at all the 10 positions.

In another preferred embodiment, the polypeptide or fragment of the invention comprises an amino acid sequence derived from SEQ ID NO:2 by introducing a mutation into SEQ ID NO:2, wherein the mutation is selected from the group consisting of: substitution of the leucine residue at position 42 by a glutamic acid residue, deletion of the serine residue at position 128, substitution of the asparagine residue at position 129 by a glutamine residue, substitution of the arginine residue at position 155 by a glutamic acid residue, substitution of the serine residue at position 179 by a glutamic acid residue, substitution of the glutamic acid residue at position 180 by a lysine residue, substitution of the serine residue at position 183 by a glutamine residue, and any combination thereof; and optionally comprising: substitution of the glycine residue at position 230 by an arginine residue, substitution of the glycine residue at position 232 by a glutamine residue, substitution of the histidine residue at position 235 by a tyrosine residue, and combinations thereof.

Any appropriate methods known in the art can be used to prepare the antigenic polypeptide or a fragment thereof derived from HIV-1 envelope protein according to the invention. For example, after determining the mutation positions and amino acid residues to be introduced, gene splicing by overlap extension PCR(SOE PCR) (Li C H, et al. 2004. Construction of middle fragment deletion mutant with improved gene splicing by overlap extension; Heckman K L, et al. 2007. Gene splicing and mutagenesis by PCR-driven overlap extension) can be used to introduce the desired mutations at corresponding positions in the coding sequence of HIV-1 envelope protein (e.g. CN54 gp145). Due to the use of primers with complementary ends in SOE PCR, the PCR products form overlapped strands, which can be then further extended in subsequent amplification reactions, and thus different amplification fragments can be overlapped and then ligated, so as to obtain the antigenic polypeptide or a fragment thereof according to the invention. Similarly, other approaches that can introduce mutations can also be used for the modification of corresponding positions, such approaches include but not limited to gene synthesis, gene recombination, gene rearrangement processes etc.

Accordingly, the invention also provides isolated polynucleotide, which comprises a nucleotide sequence that encodes the antigenic polypeptide or a fragment thereof according to the invention.

After obtaining the polynucleotide that encodes the antigenic polypeptide or a fragment thereof derived from HIV-1 envelope protein according to the invention, the polynucleotide can be inserted into a suitable expression vector, and then transformed into suitable host cell for expression, and then the resulting antigenic polypeptide or a fragment thereof according to the mention can be recovered. Expression systems that can be used in the invention to prepare the antigenic polypeptide or a fragment thereof include but not limited to: E. coli. expression systems, such as Condon strain, Gold strain; yeast expression systems; insect expression systems; phage expression systems; mammalian cell expression systems, such as CHO cell, Vero cell.

A person skilled in the art can understand that, the substitution, deletion or addition of one or more amino acids, such as conservative substitutions of amino acids, can be used to further modify the antigenic polypeptide or a fragment thereof according to the invention, with the prerequisite that the modified polypeptide or fragment should have the above mentioned amino acid mutations and is still capable of inducing protective immune response. Furthermore, besides the introduction of individual amino acid mutation, one can also further modify the antigenic polypeptide or a fragment thereof derived from HIV-1 envelope protein, including but not limited to, deletion or addition of glycosylation site, deletion or rearrangement of loop region, deletion of CFI region (the cleavage site sequence, the fusion domain, and a part of the spacer between the two heptad repeats) etc.

In another aspect, the invention provides a polypeptide vaccine comprising the above described antigenic polypeptide or fragment thereof according to the present invention together with a pharmaceutical acceptable adjuvant. Suitable adjuvants include but not limited to incomplete Freund's adjuvant, aluminum adjuvant, Bacillus Calmette-Guérin (BCG), oil-based emulsion (such as MF59 and Montanide ISA 720), immune stimulant (such as monophosphoryl lipid A), CpG oligonucleotide, saponin (such as QS21), and bacterial exotoxin-based mucosal adjuvant etc. The vaccines containing the antigenic polypeptide or a fragment thereof according to the invention can be in the form of, e.g. polypeptide vaccines, lipopeptide vaccines, dimeric or polymeric vaccines etc.

In another aspect, the invention also provides a DNA construct comprising a polynucleotide operably linked to a promoter, wherein the polynucleotide comprises a nucleotide sequence that encodes the above described antigenic polypeptide or fragment thereof according to the invention.

In preferred embodiments, the invention provides a DNA construct constructed based on gp145 amino acid sequence (SEQ ID NO:2) of HIV-1 CN54, wherein the construct encodes the antigenic polypeptide or a fragment thereof derived from HIV-1 envelope protein. In specific embodiments, the invention provides the following constructs:

Plasmid pDRVISV145M1R, carrying a polynucleotide that encodes the amino acid sequence of SEQ ID NO:2 with the leucine residue at position 42 replaced by glutamic acid residue. The antigenic polypeptide encoded by this plasmid is called "145M1R", Escherichia coli strain that contains this plasmid was deposited in CGMCC (China General Microbiological Culture collection Center, Datun Road, Chaoyang District, Beijing, China) on May 22, 2008, under the deposit number: CGMCC No. 2508;

Plasmid pDRVISV145M2R, carrying a polynucleotide that encodes the amino acid sequence of SEQ ID NO:2 with the serine residue at position 128 deleted and the asparagine residue at position 129 replaced by glutamine residue. The antigenic polypeptide encoded by this plasmid is called "145M2R", Escherichia coli strain that contains this plasmid was deposited in CGMCC on May 22, 2008, under the deposit number: CGMCC No. 2509;

Plasmid pDRVISV145M3R, carrying a polynucleotide that encodes the amino acid sequence of SEQ ID NO:2 with the arginine residue at position 155 replaced by glutamic acid residue. The antigenic polypeptide encoded by this plasmid is called "145M3R", Escherichia coli strain that contains this plasmid was deposited in CGMCC on May 22, 2008, under the deposit number: CGMCC No. 2510;

Plasmid pDRVISV145M4R, carrying a polynucleotide that encodes the amino acid sequence of SEQ ID NO:2 with the serine residue at position 179 replaced by glutamic acid residue, the glutamic acid residue at position 180 replaced by lysine residue and the serine residue at position 183 replaced by glutamine residue. The antigenic polypeptide encoded by this plasmid is called "145M4R", Escherichia coli strain that contains this plasmid was deposited in CGMCC on May 22, 2008, under the deposit number: CGMCC No. 2511;

Plasmid pDRVISV145M5R, carrying a polynucleotide that encodes the amino acid sequence of SEQ ID NO:2 with the glycine residue at position 230 replaced by arginine residue, the glycine residue at position 232 replaced by glutamine residue and the histidine residue at position 235 replaced by tyrosine residue. The antigenic polypeptide encoded by this plasmid is called "145M5R", Escherichia coli strain that contains this plasmid was deposited in CGMCC on May 22, 2008, under the deposit number: CGMCC No. 2512;

Plasmid pDRVISV1452M, carrying a polynucleotide that encodes the amino acid sequence of SEQ ID NO:2 with the leucine residue at position 42 replaced by glutamic acid residue, the serine residue at position 128 deleted and the asparagine residue at position 129 replaced by glutamine residue. The antigenic polypeptide encoded by this plasmid is called "1452M", Escherichia coli strain that contains this plasmid was deposited in CGMCC on May 22, 2008, under the deposit number: CGMCC No. 2513; and Plasmid pDRVISV1455M, carrying a polynucleotide that encodes the amino acid sequence of SEQ ID NO:2 with all the 10 mutations (i.e., the leucine residue at position 42 replaced by glutamic acid residue, the serine residue at position 128 deleted, the asparagine residue at position 129 replaced by glutamine residue, the arginine residue at position 155 replaced by glutamic acid residue, the serine residue at position 179 replaced by glutamic acid residue, the glutamic acid residue at position 180 replaced by lysine residue, the serine residue at position 183 replaced by glutamine residue, the glycine residue at position 230 replaced by arginine residue, the glycine residue at position 232 replaced by glutamine residue, the histidine residue at position 235 replaced by tyrosine residue), the antigenic polypeptide encoded by this plasmid is called "1455M", Escherichia coli strain that contains this plasmid was deposited in CGMCC on May 22, 2008, under the deposit number: CGMCC No. 2514.

As shown in the examples hereinafter, DNA constructs that respectively carry 1455M, 1452M, 145M1R, 145M2R, 145M3R, and 145M4R can all induce in BALB/c mice model the production of significantly increased specifically-binding antibodies and broad-spectrum neutralizing antibodies with high titers, and the 1455M antigen that contains all the 10 amino acid mutations can stimulate the neutralizing antibody with the broadest spectrum. It can be seen from the results of the examples hereinafter, the mutation of the leucine at position 42 replace by glutamic acid seems to be a key position among the 10 tested mutants, 145M1R, 1452M, 1455M with this mutation can all induce broad-spectrum neutralizing antibodies with high titers; but when compared to 1455M, neutralizing antibody induced by 145M1R cannot neutralize some of the tested HIV-1 clinical isolates, such as XJDC6371.

Other mutation positions M2R, M3R, M4R have same effect on increasing the broad spectrum of neutralizing antibodies.

Not intending to be limited by theories, the inventors predict that the mutation at position 42 increases the α-helical structure in envelope proteins. It has been reported that, the epitopes of cytotoxic T lymphocytes (CTL) related to the protection from vaccine are highly concentrated in the α-helical regions of various HIV-1 proteins (Yusim, K., et al. 2002. Clustering patterns of cytotoxic T-lymphocyte epitopes in human immunodeficiency virus type 1 (HIV-1) proteins reveal imprints of immune evasion on HIV-1 global variation. Journal of virology 76:8757-8768). The α-helical fragment structure induces protective CTL reaction, an effective neutralizing antibody reaction can also be similarly induced. Furthermore, the deletion of the serine residue at position 128 and the mutation at position 129 only lead to the deletion of glycosylation site but do not cause changes in secondary structure; however they can also induce broad-spectrum neutralizing antibody reaction. Based on existing publications (Koch, M., et al. 2003. Structure-based, targeted deglycosylation of HIV-1 gp120 and effects on neutralization sensitivity and antibody recognition. Virology 313:387-400), the inventors think that the deletion of glycosylation site may cause the envelope protein unable to form the oligo-glicoside chain that covers the epitopes, making some of the neutralizing epitopes on the envelope proteins exposed, so as to induce the broad-spectrum neutralizing antibody reaction.

A person skilled in the art are able to prepare antigenic polypeptides with various other combinations of the mutations, as well as the corresponding DNA construct and further test the protective effects thereof.

The present invention also provides a DNA vaccine comprising the above mentioned DNA construct together with a pharmaceutical acceptable adjuvant. After administered in vivo, DNA vaccines of the invention can express the above mentioned antigenic polypeptide or a fragment thereof according to the invention.

Moreover, the invention also provides a recombinant viral vector vaccine, which comprises a recombinant viral vector carrying a polynucleotide together with a pharmaceutical acceptable adjuvant. After administered in vivo, recombinant viral vector vaccines of the invention can express the above mentioned antigenic polypeptide or a fragment thereof according to the invention.

Recombinant viral vector vaccines that can be used in the invention include but not limited to vaccinia vector, adenovirus vector, adeno-associated virus vector, sendai virus vector, herpes simplex virus vector, human papillomavirus vector, and retroviral vector. Preferably, the recombinant viral vector is a replicative viral vector.

In a specific embodiment, the recombinant viral vector vaccine of the invention is a replicative recombinant vaccinia Tian Tan strain, which carries polypeptides encoding antigen 1455M. As shown in the examples hereinafter, using the replicative recombinant vaccinia Tian Tan strain, estimations for the immunogenicity of antigens have been carried out in BALB/c female mice model and Huntley guenea pig model. The results show that: the antigen 1455M can significantly stimulate the specific humoral immunity of BALB/c mice and guinea pigs; in particular, the produced neutralizing antibodies have broader antibody-spectrum and higher antibody titers. Furthermore, the protective antibodies can be maintains in guinea pigs for at least 6 weeks. This is by far one of the best known neutralizing antibody results obtained without adding adjuvant.

A person skilled in the art can understand that, it is also possible to insert the polynucleotides of the invention into attenuated pathogenic bacteria or symbiotic bacteria, so as to prepare recombinant bacterial vector vaccines. After administered to human, such vaccines can present and express antigens encoded therein. Accordingly, the invention also provides a recombinant bacterial vector vaccine, which comprises a recombinant bacterial vector carrying a polynucleotide together with a pharmaceutical acceptable adjuvant, the polynucleotide comprises a nucleotide sequence that encodes the above described antigenic polypeptide or fragment thereof according to the invention. Attenuated bacterial vectors that can be used in this invention include but not limited to attenuated *Salmonella, Mycobacterium bovis* (BCG), *Listeria monocytogenes, shigella, Yersinia enterocolitica, Bordetella pertussis,* and *Bacillus anthracis*. Symbiotic bacterial vectors that can be used in this invention include but not limited to *Lactobacillus, Streptococcus gordoni, Staphylococcus*.

The invention also provides a method for preventing or treating HIV-1 virus infection comprising administering the polypeptide vaccine and/or the DNA vaccine and/or the recombinant viral vector vaccine and/or the recombinant bacterial vector vaccine of the invention to a subject in need thereof.

The vaccines of the invention can be administered through any suitable immunization routes, such as patching; hypodermic, intramuscular, intravenous and intraperitoneal injection etc. Immunization strategies include mucosal immunity and cross immunity etc. A person skilled in the art can understand that, the polypeptide vaccines or DNA vaccines of the invention can be used together with such materials as lipids and nano materials etc. that can increase the presenting efficiency of antigens.

In another aspect, the invention provide antibodies, which are capable of specifically binding to a polypeptide or fragment thereof according to this invention, and has a broader and higher neutralization activity to HIV-1 virus when compared to an antibody produced by induction with a wild-type envelope protein of HIV-1.

After administering the polypeptide (or a fragment thereof) vaccines or DNA vaccines of the invention to animals, a protective immune response can be induced, which has a broad-spectrum and is against clinical isolates of various sub-types of HIV-1 from different regions. This suggests that the induced antibodies are different to most of the previous antibodies induced by natural envelope proteins. Using antibody preparation techniques known in the art like hybridoma, it is possible to utilize the polypeptides or fragments thereof or polynucleotides that encode these polypeptides or fragments of the invention to prepare monoclonal antibodies, wherein the neutralization activity of said antibodies against HIV-1 virus are higher than the antibodies produced by induction with a wild-type envelope protein of HIV-1. For example, it is possible to prepare monoclonal antibodies or antigen binding fragments thereof such as intact immunoglobulin molecules, mice-derived antibodies, humanized antibodies, chimeric antibody, scFv, Fab fragments, Fab' fragments, F(ab')2, Fv, and disulfide-linked Fv etc. These antibodies have wide application perspectives in the filed of HIV passive immunity.

Accordingly, the invention also provides a method for preventing or treating HIV-1 virus infection comprising administering the antibody of the invention to a subject in need thereof.

The invention will be further described with specific examples.

EXAMPLES

Example 1

Construction of DNA Vaccines that Contain Mutations

1. Using PCR to Introduce Mutation Positions

Recombinant plasmid pDRVISV145 (also called PT-140™/DH5a (CGMCC No. 1439)) was used as template to amplify target fragment through PCR (GeneAmp PCR System 9700 Amplifier (Applied Biosystem, USA)). Primers are as follows:

| Target fragments | Primer pairs | Primer sequences |
|---|---|---|
| 145M1R | 145M1R position upstream primer | SEQ ID NO: 9 |
| | gp145 downstream primer | SEQ ID NO: 8 |
| | gp145 upstream primer | SEQ ID NO: 7 |
| | 145M1R position downstream primer | SEQ ID NO: 10 |
| 145M2R | 145M2R position upstream primer | SEQ ID NO: 11 |
| | gp145 downstream primer | SEQ ID NO: 8 |
| | gp145 upstream primer | SEQ ID NO: 7 |
| | 145M2R position downstream primer | SEQ ID NO: 12 |
| 145M3R | 145M3R position upstream primer | SEQ ID NO: 13 |
| | gp145 downstream primer | SEQ ID NO: 8 |
| | gp145 upstream primer | SEQ ID NO: 7 |
| | 145M3R position downstream primer | SEQ ID NO: 14 |
| 145M4R | 145M4R position upstream primer | SEQ ID NO: 15 |
| | gp145 downstream primer | SEQ ID NO: 8 |
| | gp145 upstream primer | SEQ ID NO: 7 |
| | 145M4R position downstream primer | SEQ ID NO: 16 |
| 145M5R | 145M5R position upstream primer | SEQ ID NO: 17 |
| | gp145 downstream primer | SEQ ID NO: 8 |
| | gp145 upstream primer | SEQ ID NO: 7 |
| | 145M5R position downstream primer | SEQ ID NO: 18 |

Reaction system: Plasmid template 0.5 μl, Pyrobest Taq (5 U/μl) 0.5 μl (Takara), 10× Pyrobest Taq Buffer (MgCl2 added) 5 μl, dNTP (2.5 mM) 4 μl, upstream primer 1 μl, downstream primer 1 μl, adding $ddH_2O$ to 50 μl (200 μl PCR tube with protuberant cap, Axygen). Reaction conditions: 94° C. 5 min predenature; 94° C. 50 seconds, annealing temperature 50 seconds, 72° C. 2 min, for 35 cycles; 72° C. extension 10 min. Only gp145 upstream primer/145M3R position downstream primer use 60° C. as annealing temperature; the others primers all use 65° C. as annealing temperature. The resulting target gene is recovered from gel (Omega E.Z.N.A. Gel Extraction Kit E.Z.N.A Cycle-Pure Kit). Using the two gene fragments corresponding to each mutation position as template, gp145 upstream primer and gp145 downstream primer as primers, the target gene was amplified through PCR. Reaction system: plasmid template each 0.5 μl, Ex Taq (5 U/μl) 0.5 μl, 10× Ex Taq Buffer (MgCl2 added) 5 μl, dNTP (2.5 mM) 4 μl, upstream primer 1 μl, downstream primer 1 μl, adding $ddH_2O$ to 50 μl. Reaction conditions: 94° C. 5 min predenature; 94° C. 50 seconds, 68° C. 50 second, 72° C. 2 min, for 35 cycles; 72° C. extension 10 min. The 5 resulting target gene fragments were recovered from gel: 145M1R, 145M2R, 145M3R, 145M4R and 145M5R. Using 145M1R as template, 145M2R position upstream primer and gp145 downstream primer, gp145 upstream primer and 145M2R position downstream primer as primer pairs, the target fragments were amplified through PCR, using the same conditions as above. Then using the 2 target gene fragments recovered from gel as template, gp145 upstream primer and gp145 downstream primer as primers, target gene with the second mutation position was amplified through PCR, using the same conditions as above. The 1452M fragment (containing 145M1R and 145M2R) was recovered from gel. Using 1452M as template, same method as above, a further PCR was performed to introduce mutations. As such, until the 1455M fragment with all the 10 mutations introduced was obtained.

2. Restriction enzymes EcoR V and BamH I (Takara) were used to digest HIV-1 CN54 145M1R, 145M2R, 145M3R, 145M4R, 145M5R, 1452M, 1455M and DNA vaccine vector pDRVISV1.0 (CN1560259 (China Patent Application: 200410028280.3); and Haishan Li, et al. Enhancement of Gag-Specific Immune Responses Induced by DNA Vaccination by Incorporation of a 72-bp element from SV40 Enhancer in the Plasmid Vector. Chinese Medical Journal (English) 2007; 120 (6):496-502). Digestion system: plasmids or target genes 10 μl, EcoR V 2 μl, BamH I 2 μl, 10× BamH I buffer K 5 μl, adding $ddH_2O$ till a total volume 50 μl, 37° C. incubation for 4 h, agarose (GIBCO) gel electrophoresis was performed for separation. Fragment with corresponding size (the inserted target gene fragment is about 2.1 kb, the vector fragment is about 5 kb) was cut for agarose gel recovery (Omega, E.Z.N.A. Gel Extraction Kit E.Z.N.A Cycle-Pure Kit).

3. Ligation reaction system: 2× Rapid Ligation Buffer (NEB) 5 μl, the recovered product of synthetic target gene fragment 3 μl, the recovered product of vector fragment T4 DNA ligase (NEB) 1 μl, were allowed for ligation at 4° C. for 8 hours. The ligation products are transformed to *E. coli*. DH5α competent cells (Takara), spreaded on plate (Qingdao α Medical Mechine) with kanamycin sulfate (Beijing 2$^{nd}$ Pharm.), 37° C. incubation for 16 h. Monoclonal colonies were picked and inoculated into 3 ml LB medium (Amersham) with 60 μg/ml kanamycin, and cultured at 37° C. for 16 h, shaken at 200 rpm (HZQ-X100 Culture Shaker from Harbin). Omega E.Z.N.A. Plasmid Miniprep Kit I was used to extract mini-preparations of plasmids. After digestion with enzymes, PCR identification, correctly identified plasmids were sent to Invitrogen for sequencing confirmation. Correctly identified plasmids were named as: pDRVISV145M1R, pDRVISV145M2R, pDRVISV145M3R, pDRVISV145M4R, pDRVISV145M5R, pDRVISV1452M and pDRVISV1455M. For enzyme digestion results see FIG. 1; PCR identification results see FIG. 2; it can be seen from the Figures that the constructed plasmids all have correctly inserted target genes.

4. Immunoblot Assay of the Expression of Inserted Target Genes

1) Transfected 293T cells (purchased from ATCC) were collected by 10000 rpm centrifugation (Sigma) to prepare protein samples which were then run on 10% SDS-PAGE electrophoresis; ((29:1) Acrylamide from SIGMA; Hoefer EPS 2A200 and PowerPAC1000 both from Bio-Rad);

2) Whatman filter paper (Whatman) was cut into same size as the gel, 3 pieces soaked in positive electrode solution, pieces soaked in negative electrode solution; (10× electrotransfer buffer stock: 0.25M Tris (Sigma), 1.92M Glycine (Sigma), 1% SDS (Sigma), pH8.3; positive electrode solution: 7 volumes of stock, 2 volumes of methanol, 1 volume $ddH_2O$; negative electrode solution: 1 volume stock, 9 volumes $ddH_2O$);

3) After electrophoresis at constant voltage 120 V for 45 min, the gel was soaked in negative electrode solution;

4) PVDF membrane (Sigma) was soaked in methanol for 15 seconds, then washed with deionized water for 4 times, and then the PVDF membrane was placed in the positive electrode solution and soak for 10 min;

5) From the negative electrode to the positive electrode, negative electrode filter paper, gel, PVDF membrane, positive electrode filter paper were placed in this order onto electo-transfer instrument (Bio-Rad), be careful to remove any bubbles between different layers, 10 mA constant stream for 45 min;

6) PVDF membrane was taken out and then placed into deionized water and washed 3 times;

7) The membrane was then placed into PBS solution with 5% skim milk and blocked for 12 h at 4° C.;

8) The membrane was then placed into PBST and washed 3 times, then placed into blocking solution with 1% HIV-1 positive serum, at room temperature for 2 h, PBST washing 5 times;

9) Then the membrane was placed into sheep-anti-human IgG-HRP (Zhongshan Jinqiao, Beijing) which was 1:2000 diluted using PBS solution with 5% skim milk, room temperature for 1 hour, PBST washing 5 times;

10) Adding color development solution (18 ml ddH$_2$O, 2 ml NiCl$_2$, 200 μl 1M pH7.6 Tris-HCl, DAB (Sigma) 6 mg, H$_2$O$_2$ 30 μl), developing at room temperature for 10 min, washing with distilled water to terminate the reaction.

The expression identification results of DNA constructs can be seen in FIG. 3. The results indicate that: all the 7 antigens can be correctly expressed.

Example 2

Construction of Recombinant Tian Tan Strains Using the Mutants

1. The Construction of Shuttle Plasmid pSC65 (Deposited as: CGMCC No. 1097)

Restriction enzymes Xba I and Pml I (Takara) were used to cut HIV-1 CN54 gp145 and 1455M genes from sequencing-confirmed pDRVISV145 and pDRVISV1455M respectively, after gel purification, high fidelity Taq (Takara) was conducted to extend and make the ends blunt; then linked by blunt end ligation process into Sma I (Takara) mono-digested and dephosphorylated pSC65 vector. High fidelity Taq reaction system: Pyrobest Taq 0.5 μl, dNTP (Takara) 1 μl, 10× Pyrobest Taq Buffer (MgCl$_2$ added) 1 μl, adding deionized water to 10 μl. Reaction condition was: 72° C., 5 min. CIP (NEB) dephosphorylation system: CIP 1 μl, NEB buffer 3 2 μl, deionized water 7 μl. The ligation product was used to transform *E. coli*. DH5a competent cells, and then spreaded on plate with kanamycin sulfate, cultured at 37° C. for 16 h. Monoclonal colony was picked and inoculated into 3 ml LB medium (Amersham) with 50 μg/ml penicillin, cultured at 37° C. for 18 h, shaken at 200 rpm. The plasmids were then subjected to enzyme identification and PCR identification, correctly identified plasmids were named as pSC145 and pSC1455M, respectively. *Escherichia coli* strain that contains plasmid pSC1455M was deposited in CGMCC on May 22, 2008, under the deposit number: CGMCC No. 2515. After identification, the two shuttle plasmids were correctly constructed.

2. Construction, Purification and Amplification of Recombinant Vaccinia Tian Tan Strain 1) vaccinia Tian Tan strain (Purchased from National Vaccine and serum Institute, Beijing) was used in a dose of 0.1 MOI (multiplicity of infection) to infect 143B cells (purchased from ATCC), incubated at 37° C. for 1 hour;

2) Adding 250 μl Eagle's medium without serum or antibiotics (purchased from China Center for Disease Control and Prevention) into each of two Eppendorf tubes (Axygen), adding 8 μg plasmid pSC145 or pSC1455M into one of the tube, mixed; adding 10 μl Lipofectamine 2000 transfection agent (Invitrogen) into another tube, mixed; incubation at room temperature for 5 min;

3) Mixing the solutions of the two Eppendorf tubes, place at room temperature for 30 min;

4) Using 5 ml Eagle's medium without serum or antibiotics to wash the cells for 2 times, and then adding 3 ml Eagle's medium without serum or antibiotics;

5) Adding the mixture of DNA plasmids and Lipofectamin2000 into T25 cell culture flask (Corning Costar), incubate at 37° C. in CO2 incubator (SANYO);

6) 4 h later, using 4 ml Eagle's maintaining medium to change the solution, then incubating at 37° C. in CO2 incubator, incubating for another 48 h and then using low melting temperature agarose (Gibco) for plaque selection;

7) Preparing the low melting temperature agarose: 2% low melting temperature agarose, adding same volume of 2× Eagle's complete medium (purchased from China Center for Disease Control and Prevention), adding X-gal (Promega) to final concentration of 200 μg/ml, adding Neutral Red (purchased from China Center for Disease Control and Prevention) to final concentration of 50 μg/ml, slightly pipetting, avoiding the formation of bubbles;

8) Carefully pouring the medium in the flask, slowly adding 40° C. plaque solution, waiting until the solution was solidified and then placing the flask into 37° C. CO2 incubator (SANYO);

9) Incubating for 4 h and then observing whether the cell present blue plaques;

10) Picking blue plaque, and then adding it to 500 μl Eagle's maintaining solution, repeatedly freezing and thawing for 3 times and then storing for future use;

11) Pipetting 200 μl of the above mentioned solution that has been repeatedly frozen and thawed for 3 times, adding it in to 80%-90% smeared 143B cells, incubating at 37° C. in CO2 incubator for 48 h, observing the plaque situation, performing the plaque selection and picking again, repeating in this way until more than 5 generations, the resulting purified recombinant vaccinia virus rTV145 and rTV1455M were obtained;

12) Discarding the Eagle's medium with 10% bovine serum (Gibco) for Chicken Embryo cell cultures, and changing to half volume of Eagle's maintaining medium with 2% bovine serum. Using the dose of 5MOI to infect Chicken Embryo cells, after mixing, incubating it at 37° C. in 5% CO2 incubator; 2 h later, supplementing the other half volume of Eagle's maintaining medium with 2% bovine serum, then incubating at 37° C. in 5% CO2 incubator (SANYO);

13) 48 h later, discarding the cell culture medium, using sterile PBS to wash once, using 1 ml PBS to collect virus, repeatedly freezing and thawing twice and then storing in aliquotes in −80° C. fridge (SANYO).

Purified recombinant virus was identified with PCR and immunoblot. Results are shown in FIGS. 5 & 6. The results show that, the constructed recombinant vaccinia can correctly express the inserted gp145 and 1455M genes.

Example 3

Comparison Assay of the Immunogenicity of the Modified Antigens

1. Experimental Animals and Immunizing Protocol

BALB/c female mice (H-2d), 6-8 weeks old, weight 18-25 gram, were purchased from the Institute of Laboratory Animal Science, Chinese Academy of Medical Sciences, and were grown in The Institute of Laboratory Animal Science, Chinese Academy of Medical Sciences.

Huntley female guinea pigs, 6-8 weeks old, 180 g-220 g, were purchased from National Institute for the Control of Pharmaceutical and Biological Products, and were grown in The Institute of Laboratory Animal Science, Chinese Academy of Medical Sciences.

7 BALB/c female mice per group were immunized with DNA vaccines at the 0, 2, 4, 6 week respectively, at the 9th week blood samples were taken from eye, the whole blood was incubated at 37° C. for 1 h, and then centrifuged at 3000 rpm to separate serum for examination. 4 Huntley female guinea pigs per group were immunized with DNA vaccines at the 0, 2, 4 week respectively, at the 10th week vaccinia strengthening immunization was performed, at the 14th, 16th week, blood samples were taken from heart, the whole blood was incubated at 37° C. for 1 h, and then centrifuged at 3000 rpm to separate serum for examination.

Each mouse was intramuscularly injected at tibialis anterior with 100 μg DNA vaccine (1 mg/ml), each hind leg with 50 μg. Huntley female guinea pig was intramuscularly injected 250 μg (1 mg/ml) at each hind leg, the immuinizing dose of vaccinia was 1×10$^7$ PFU (Plaque forming unit).

2. ELISA Assay of Specifically Binding Antibodies

1) Using coating solution (Na$_2$CO$_3$ 1.59 g (Sigma), NaHCO$_3$ 2.93 g (Sigma), adding deionized water to 1000 ml, mixed and then kept at 4° C.) to dilute HIV-1 CN54 envelope protein gp120 antigen (Expressed, purified and prepared in our group, the purity is higher than 90%; the preparation method can be found in master thesis of Jie Feng "The expression purification and primary application of recombinant HIV-1 envelope glycoprotein gp120 and gp4") to about 5 μg/ml, adding to 96-well palte (Corning Costar) at 100 μl/well, 4° C. coating for 12 h, 1×PBS washing 3 times, adding 200 μl coating solution (PBST formulated 5% BSA (Sigma)) to each well, 37° C. incubate for 1 h.

3) 1×PBST washing 3 times, immunity mice sera were double diluted in two series starting from 1:100 and 1:200 respectively, adding 100 μl of serial dilutedsera to each well, and each plate had 2 empty, 2 positive control and 2 negative control wells, 37° C. incubation for 1 h.

4) 1×PBST washing 5 times, adding 100 μl 1:2000 diluted sheep-anti-mice IgG-HRP, 37° C. incubation for h.

5) 1×PBST washing 5 times, adding 100 μl OPD color development substrate (Sigma), develop at room temperature for 15 min in dark.

6) Adding 50 μl 2M sulfate (purchased from Beijing Chemical Agent Company) to each well to terminate the reactions, using ELISA Reader (Thermo Electron Corporation Multiscan ascent plate reader 354) to detect the absorption (A) value for each well at 492 nm wave length. If the absorption of experiment well/control well was larger than 2:1, then the well was determined as positive well.

The results are shown in FIG. 6. The results show that, the average specifically-binding antibody titer stimulated by 1455M DNA vaccine alone is much higher than that stimulated by gp145 DNA vaccine; the antibody titer is increased for more than 3.5 fold (p=0.0020). Additionally, it is confirmed in further experiment that, the increase of binding antibody is caused by mutations contained in 1452M; 1452M vaccine can induce much higher average binding antibody titer than gp14, the average antibody titer thereof can reach up to 2400, the highest average titer can reach 9600. While other vaccines like 145M3R, 145M4R, 145M5R do not increase antibody titer after immunization, on the contrary the binding antibody reaction intensity is somehow decreased. The data of the third experiment show that, 145M1R vaccine can induce similar binding antibody titer like 1452M vaccine; through statistic analysis, it has been shown that two groups of specifically-binding antibody titer are significantly higher than unaltered gp145 (p=0.0177, N=8; p=0.0083, N=8). And the data show that the antibody titer induced by 145M1R is slightly higher than that of 1452M vaccine group, the reaction intensity thereof shows extremely significant difference (p=0.0083, N=8). Two experimental results of primates and one clinical experimental result suggest that specifically-binding antibody relates to immune protection. Our altered antigen 1455M (containing all the 10 amino acid mutation positions), 1452M, 145M1R can all significantly increase the reaction intensity of specifically-binding antibody from BALB/c mice.

3. BALB/c Female Mice and Serum Antibody Neutralization Examination

1) Each group of BALB/c sera is mixed with equal volume; the mice sera and guinea pig sera to be tested are sterilized at 56° C. for half an hour;

2) Take 15 μl serum and adding to 135 μl DMEM medium that contains 1 μM indinavir (Gibco); and then perform 2 times' (mice sera), 3 times' (guinea pig sera) gradient dilution;

3) Adding 50 μl 200 TCID50 virus to each well, incubate in CO$_2$ incubator at 37° C. for 1 h;

4) Adding 1×104 TZM-bl cell (purchased from ATCC) to each well, incubate in CO$_2$ incubator at 37° C. for 48 h;

5) Discard the medium in each well, adding 200 μl PBS to wash each well twice; adding 50 μl diluted cell lysis (Promega, E1531) to each well; when the cells are completely lysed under microscope (IX70 fluorescence microscope: OLYMPUS), transfer the lysis into 96-weel data reader plate (PerkinElmer Life Sciences flat-bottomed 96-well plate). Adding formulated 100 μl luciferase substrate (Bright-Glo substrate and buffer) (Promega, E1501) to each well, finish the seld-emmision fluorescence detection (Victor 3 luminometer, PerkinElmer).

6) Us the formula [1−(Experiment group RLU-cell control RLU)/(control group RLU-cell control RLU)]×100% to calculate RLU pad value; if the value is larger than 50%, then the neutralization reaction of the serum in such dilution is determined as positive.

See Table 3 for the results of BALB/c female mice serum antibody neutralization examination

TABLE 3

The results of BALB/c female mice serum antibody neutralization assay

| Vaccine groups | Neutralization titer against HIV-1 isolates | | | | | |
|---|---|---|---|---|---|---|
| | XJDC6371 | XJDC6431 | XJDC0793 | CBJB105 | CBJB248 | 020101300 |
| pDRVISV145 | <6 | <6 | <6 | <6 | <6 | 12 |
| pDRVISV1455M | 12 | 24 | 24 | 24 | 24 | 12 |
| pDRVISV1452M | <6 | 24 | 24 | 24 | 24 | 24 |

TABLE 3-continued

The results of BALB/c female mice serum antibody neutralization assay

| Vaccine groups | Neutralization titer against HIV-1 isolates | | | | | |
|---|---|---|---|---|---|---|
| | XJDC6371 | XJDC6431 | XJDC0793 | CBJB105 | CBJB248 | 020101300 |
| pDRVISV145M1R | <6 | 24 | 24 | 24 | 24 | 24 |
| pDRVISV145M2R | <6 | 12 | 12 | 12 | 12 | 12 |
| pDRVISV145M3R | <6 | <6 | <6 | <6 | 12 | 12 |
| pDRVISV145M4R | <6 | <6 | <6 | <6 | 12 | 12 |
| pDRVISV145M5R | <6 | <6 | <6 | <6 | <6 | <6 |

The modified antigen 1455M can induce a broadest spectrum protection (which can neutralize all the clinical isolates of if and B'/C subtypes from Xinjiang, Beijing and Anhui), and can neutralized all the virus with high titer (neutralizing titers to all isolates are larger than 1:12); unmodified gp145 can only neutralize one B' subtype virus, and has no neutralizing to other isolates. Antibodies induced by antigens 1452M and 145M1R can effectively neutralize most of the clinical isolates with broad spectrum, but the broad spectrum cannot compete with 1455M group. 145M2R antigen can induce antibodies with broad-spectrum neutralizing activity; the intension of the neutralizing antibody with the position mutated is around 1:12. 145M3R and 145M4R antigens can induce a broader-spectrum for neutralizing antibody.

The results show that the antigen 1455M containing 10 amino acid mutations can significantly broaden the spectrum, increase reaction intensity of neutralizing antibody. It is found through further researches that the induced protective reactions are mainly caused by 1452M that contains the first two mutation regions, and it is finally found out that the induced protective reactions are mainly caused by the first mutation 145M1R. Other mutations like 145M2R, 145M3R, 145M4R etc. can also induce a broad-spectrum for neutralizing antibody.

The sera neutralizing results of Huntley guinea pigs at the $14^{th}$, $16^{th}$ week are shown in FIGS. 7, 8, 9, 10.

FIGS. 7 & 8 show that: 1455M antigen induces most of the guinea pigs in the group to produce broad-spectrum (against all the 8 clinical isolates of HIV) neutralizing antibody, and the reaction can last for at least 6 weeks. This means that the antigen can similarly induce broad-spectrum long-lasting neutralizing antibody protection against various subtypes of HIV in human.

FIGS. 9 & 10 show that 1455M antigen induces most of the guinea pigs in the group to produce neutralizing antibody with high titer (against all the 8 clinical isolates of HIV), the highest titer can reach 1:270; and the reaction can last for at least 6 weeks. This means that the antigen can similarly induce broad-spectrum long-lasting neutralizing antibody protection against various subtypes of HIV in human.

The above examples are only for illustrating purpose, with no intention to limit this invention. It is clear that, based on the substantial principle of the invention, a person skilled in the art can make various changes and modifications to this invention, therefore, these changes and modifications are also included in the scope of the invention.

What is claimed is:

1. An antigenic polypeptide or a fragment thereof derived from HIV-1 envelope protein, wherein the polypeptide or fragment comprises an amino acid sequence containing at least the mutation of substitution of the leucine residue at the position corresponding to position 52 in SEQ ID NO:1 by a glutamic acid or an aspartic acid residue.

2. The antigenic polypeptide or fragment thereof according to claim 1, wherein the amino acid sequence contains at least the following mutations:
   the substitution of the leucine residue at the position corresponding to position 52 in SEQ ID NO:1 by a glutamic acid or an aspartic acid residue;
   the deletion of the threonine residue at the position corresponding to position 138 in SEQ ID NO:1; and
- the substitution of the asparagine residue at the position corresponding to position 139 in SEQ ID NO:1 by a glutamine residue.

3. The antigenic polypeptide or fragment thereof according to claim 1, wherein the amino acid sequence contains the following mutations:

- substitution of the leucine residue at a position corresponding to position 52 in SEQ ID NO:1 by a glutamic acid or an aspartic acid residue;
- deletion of the threonine residue at a position corresponding to position 138 in SEQ ID NO:1;
- substitution of the asparagine residue at a position corresponding to position 139 in SEQ ID NO:1 by a glutamine residue;
- substitution of the arginine residue at a position corresponding to position 166 in SEQ ID NO:1 by a glutamic acid or an aspartic acid residue;
- substitution of the isoleucine residue at a position corresponding to position 184 in SEQ ID NO:1 by a glutamic acid or an aspartic acid residue;
- substitution of the aspartic acid residue at a position corresponding to position 185 in SEQ ID NO:1 by a lysine, an arginine or a histidine residue;
- substitution of the serinethreonine residue at a position corresponding to position 188 in SEQ ID NO:1 by a glutamine or an asparagine residue;
- substitution of the glycine residue at a position corresponding to position 235 in SEQ ID NO:1 by an arginine, a lysine or a histidine residue;
- substitution of the glycine residue at a position corresponding to position 237 in SEQ ID NO:1 by a glutamine or an asparagine residue; and
- substitution of the threonine residue at a position corresponding to position 240 in SEQ ID NO:1 by a tyrosine residue.

4. The antigenic polypeptide or fragment thereof according to claim 1, wherein the HIV-1 envelope protein is selected from the group consisting of gp120, gp128, gp140, gp140TM, gp145, gp150, gp160, and an equivalent thereof.

5. The antigenic polypeptide or fragment thereof according to claim 1, wherein the HIV-1 envelope protein is gp145 of HIV-1 CN54 having the amino acid sequence of SEQ ID NO:2.

6. An antigenic polypeptide or a fragment thereof derived from HIV-1 envelope protein, wherein the polypeptide or fragment thereof comprises an amino acid sequence derived from SEQ ID NO:2 by introducing a mutation into SEQ ID NO:2, and wherein the amino acid sequence contains at least the mutation of substitution of the leucine residue at position 42 by a glutamic acid residue.

7. The antigenic polypeptide or fragment thereof according to claim 6, wherein the amino acid sequence contains at least the following mutations:

- substitution of the leucine residue at position 42 by a glutamic acid residue;
- deletion of the serine residue at position 128; and
- substitution of the asparagine residue at position 129 by a glutamine residue.

8. The antigenic polypeptide or fragment thereof according to claim 6, wherein the amino acid sequence contains the following mutations:

- substitution of the leucine residue at position 42 by a glutamic acid residue;
- deletion of the serine residue at position 128;
- substitution of the asparagine residue at position 129 by a glutamine residue;
- substitution of the arginine residue at position 155 by a glutamic acid residue;
- substitution of the serine residue at position 179 by a glutamic acid residue;
- substitution of the glutamic acid residue at position 180 by a lysine residue;
- substitution of the serine residue at position 183 by a glutamine residue;
- substitution of the glycine residue at position 230 by an arginine residue;
- substitution of the glycine residue at position 232 by a glutamine residue; and
- substitution of the histidine residue at position 235 by a tyrosine residue.

9. The antigenic polypeptide or fragment thereof according to claim 1 or 6, which further contains substitution, deletion or addition of one or more amino acids, and the polypeptide or fragment thereof is capable of inducing an immune response.

10. The antigenic polypeptide or fragment thereof according to claim 1 or 6, which further contains a modification selected from the group consisting of deletion or addition of glycosylation site, deletion or rearrangement of loop region, deletion of CFI region, and combination thereof.

11. A polypeptide immunogen comprising a polypeptide or fragment thereof according to claim 1 or 6 together with a pharmaceutical acceptable adjuvant and/or carrier.

12. A method for treating HIV-1 virus infection comprising a step of administering the polypeptide immunogen of claim 11 to a subject in need thereof.

\* \* \* \* \*